US011866788B2

(12) United States Patent
Bagchi et al.

(10) Patent No.: US 11,866,788 B2
(45) Date of Patent: Jan. 9, 2024

(54) ROLE OF PVT1 IN THE DIAGNOSIS AND TREATMENT OF MYC-DRIVEN CANCER

(71) Applicant: Sanford Burnham Prebys Medical Discovery Institute, La Jolla, CA (US)

(72) Inventors: Anindya Bagchi, San Diego, CA (US); Ashutosh Tiwari, San Diego, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 138 days.

(21) Appl. No.: 17/053,328

(22) PCT Filed: May 8, 2019

(86) PCT No.: PCT/US2019/031349
§ 371 (c)(1),
(2) Date: Nov. 5, 2020

(87) PCT Pub. No.: WO2019/217572
PCT Pub. Date: Nov. 14, 2019

(65) Prior Publication Data
US 2021/0071266 A1  Mar. 11, 2021

Related U.S. Application Data

(60) Provisional application No. 62/668,638, filed on May 8, 2018.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,373,071 A | 2/1983 | Itakura |
| 4,401,796 A | 8/1983 | Itakura |
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,973,679 A | 11/1990 | Caruthers et al. |
| 5,047,524 A | 9/1991 | Andrus et al. |
| 5,132,418 A | 7/1992 | Caruthers et al. |
| 5,153,319 A | 10/1992 | Caruthers et al. |
| 5,204,253 A | 4/1993 | Sanford et al. |
| 5,262,530 A | 11/1993 | Andrus et al. |
| 5,279,833 A | 1/1994 | Rose |
| 5,683,898 A | 11/1997 | Yazawa et al. |
| 5,700,642 A | 12/1997 | Monforte et al. |
| 2004/0023267 A1 | 2/2004 | Morris |
| 2009/0098622 A1 | 4/2009 | Facciotti et al. |
| 2009/0311748 A1 | 12/2009 | Isogai et al. |
| 2013/0230547 A1 | 9/2013 | Sanda et al. |
| 2018/0110788 A1 | 4/2018 | Toyoshima et al. |
| 2019/0117751 A1 | 4/2019 | Torigoe et al. |

FOREIGN PATENT DOCUMENTS

| | | |
|---|---|---|
| CN | 108220434 A | 6/2018 |
| CN | 106047880 B | 2/2019 |
| WO | WO-2019053003 A1 | 3/2019 |
| WO | WO-2019217572 A1 | 11/2019 |
| WO | WO-2021055846 A1 | 3/2021 |

OTHER PUBLICATIONS

L'Abbate et al (MYC-containing amplicons in acute myeloid leukemia: genomic structures, evolution, and transcriptional consequences, Leukemia, vol. 32, 2018), (Year: 2018).*
Verduci et al (The oncogenic role of circPVT1 in head and neck squamous cell carcinoma is mediated through the mutant p53/YAP/TEAD transcription-competent complex, Genome Biology, vol. 18, 2017), (Year: 2017).*
Xiao (Prognostic values of long noncoding RNA PVT1 in various carcinomas: An updated systematic review and meta-analysis, Cell proliferation, vol. 41, 2018) (Year: 2018).*
Tashiro et al (Role of long non-coding RNA PVT1 in regulating MYC in human cancer, Abstract. Journal of Urology, vol. 197, 2017) (Year: 2017).*
Felgner et al., Lipofection: A highly efficient, lipid-mediated DNA-transfection procedure, Proc. Natl. Acad. Sci. USA 84: 7413-7414 (1987).
Mannino et al. Liposome mediated gene transfer. BioTechniques 6(7):682-690 (1988).
PCT/US2020/051626 International Search Report and Written Opinion dated Feb. 1, 2021.
Prive et al., Identification and characterization of three novel lipases belonging to families II and V from Anaerovibrio lipolyticus 5ST. PLoS One 8(8):e69076 [1-9] (2013).
Szoka et al., Comparative properties and methods of preparation of lipid vesicles (liposomes). Annual Review of Biophysics and Bioengineering 9:467-508 (1980).
Cavalli et al. Intertumoral Heterogeneity within Medulloblastoma Subgroups. Cancer Cell 31:737-754 (2017).
PCT/US2019/031349 International Invitation to Pay Additional Fees dated Jul. 29, 2019.
PCT/US2019/031349 International Search Report and Written Opinion dated Oct. 16, 2019.

(Continued)

*Primary Examiner* — Laura B Goddard
*Assistant Examiner* — Sarah A Alsomairy
(74) *Attorney, Agent, or Firm* — WILSON SONSINI GOODRICH & ROSATI

(57) ABSTRACT

Disclosed herein are methods of diagnosing and treating MYC-driven cancers by detecting a PVT1 splice variant in a biological sample from a subject.

9 Claims, 37 Drawing Sheets

Specification includes a Sequence Listing.

(56) References Cited

OTHER PUBLICATIONS

Tashiro et al. MP99-18 Role of long non-coding RNA PVT1 in regulating MYC in human cancer. Journal of Urology 197(4S):e1327-e1328 (2017).
Tseng et al. PVT1 dependence in cancer with MYC copy-number increase. Nature 512(7512):82-86 (2014).

* cited by examiner

Fig. 4
Splice Variants Expression in MB PDX samples
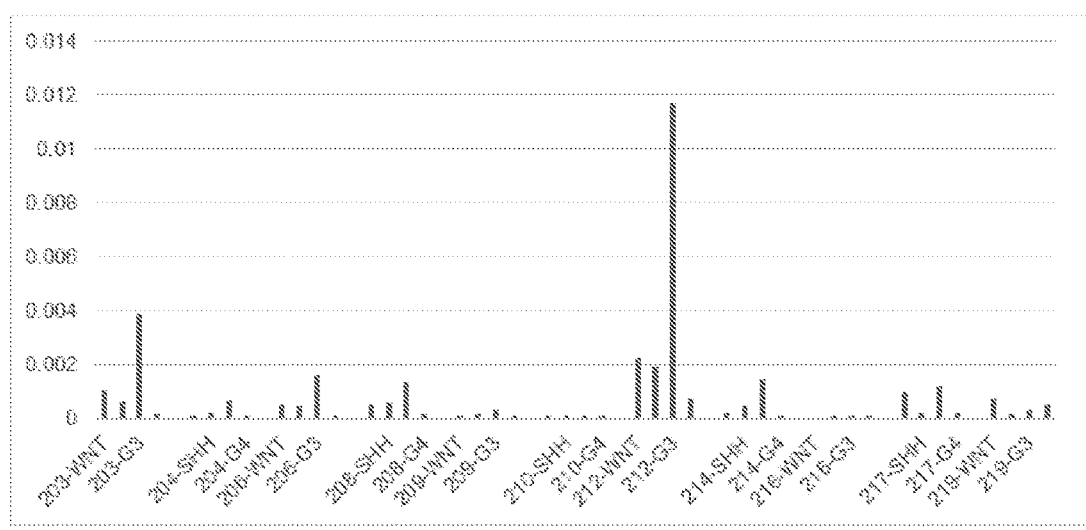
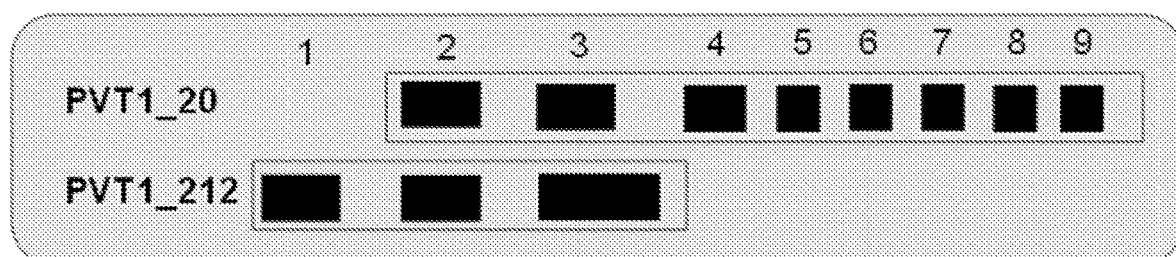

Fig. 5
PVT1_212 Expression in Medulloblastoma PDX
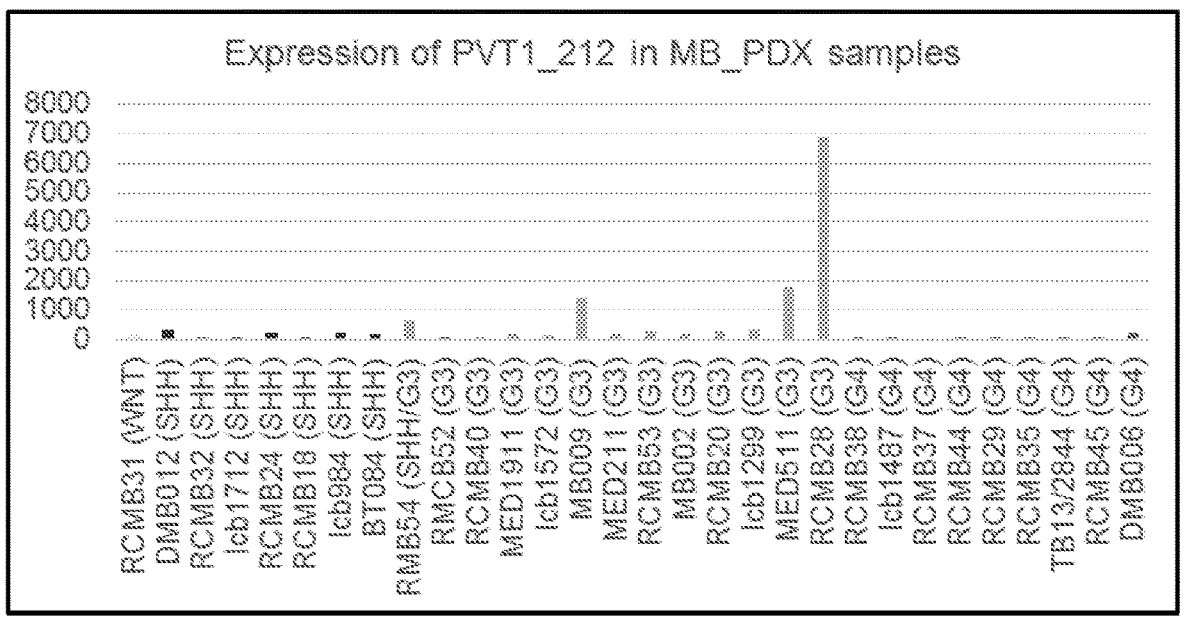
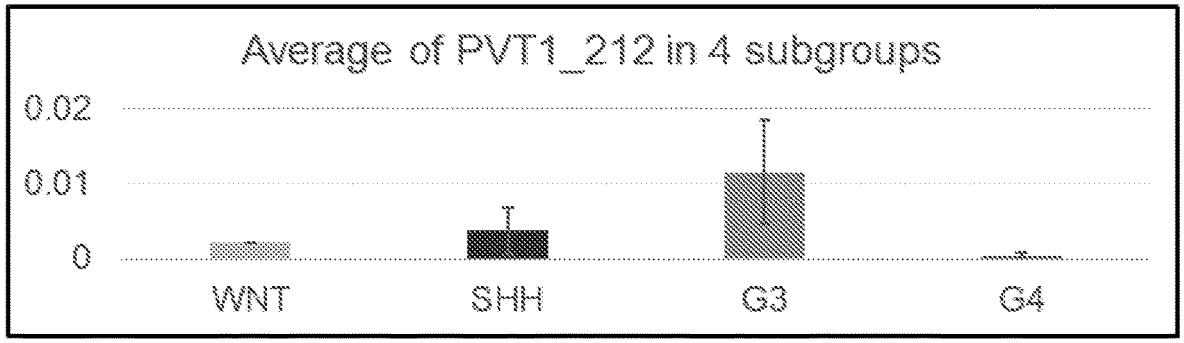

Fig. 6
Expression of PVT1_212 in Medulloblastoma-PDX samples
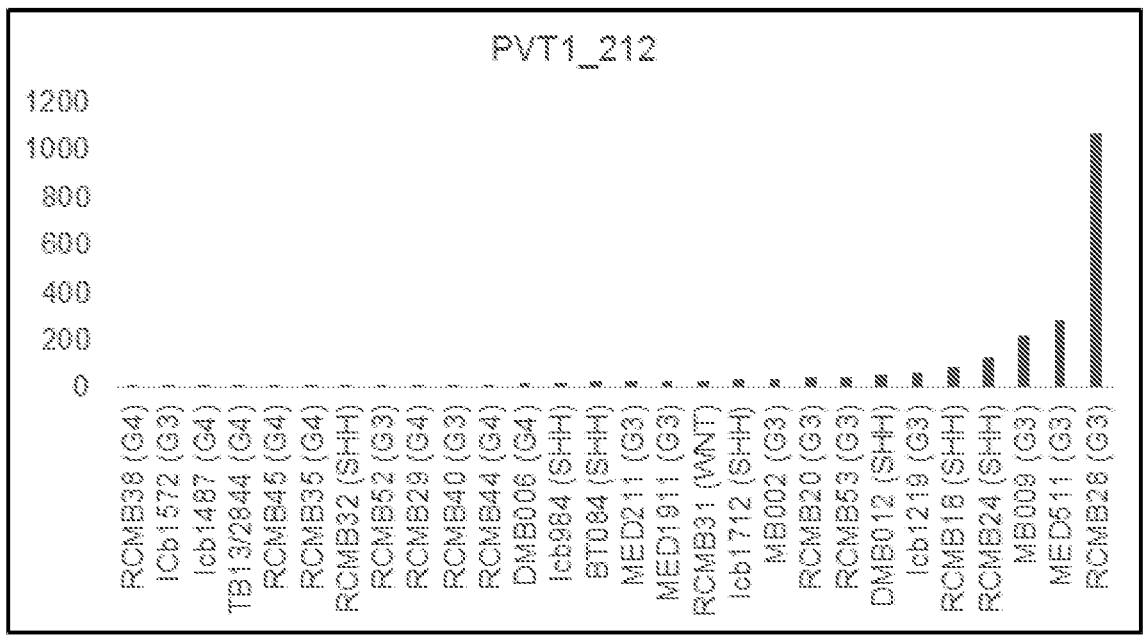
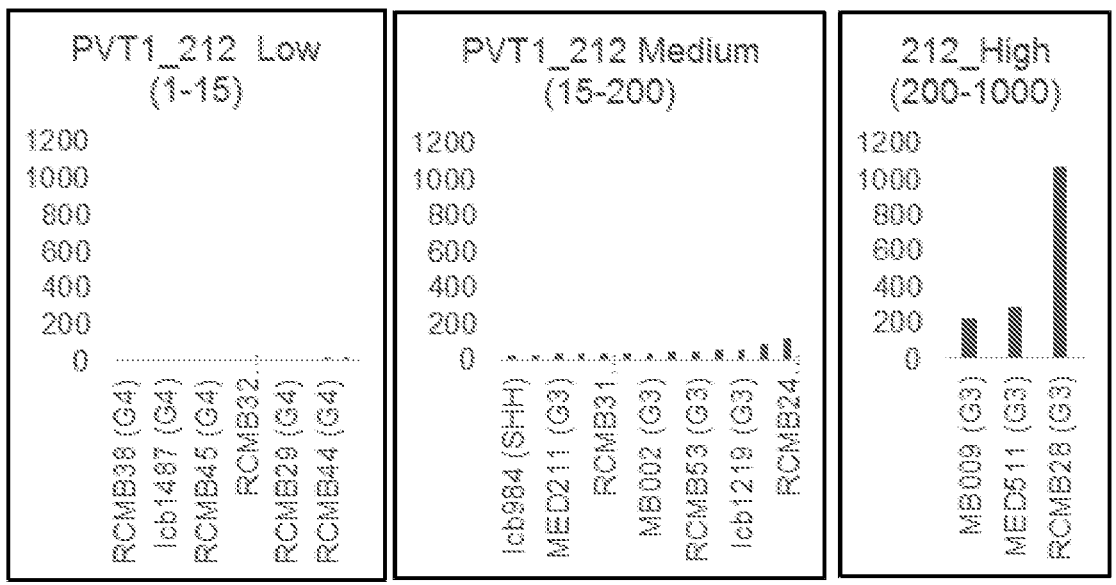

Fig. 8
siPVT1 for SKBR3
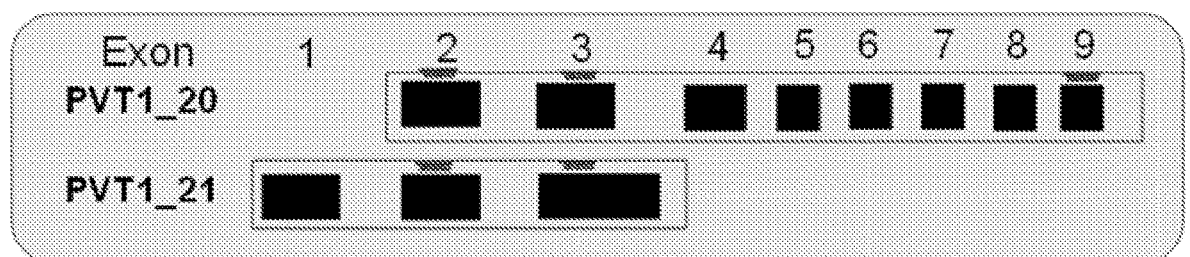
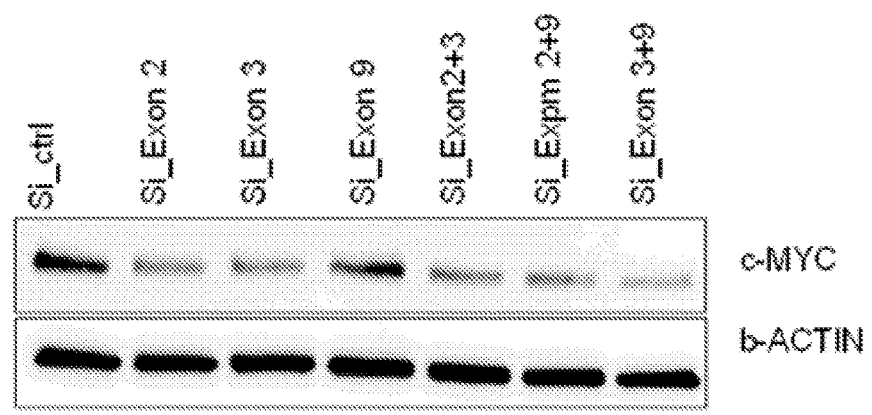
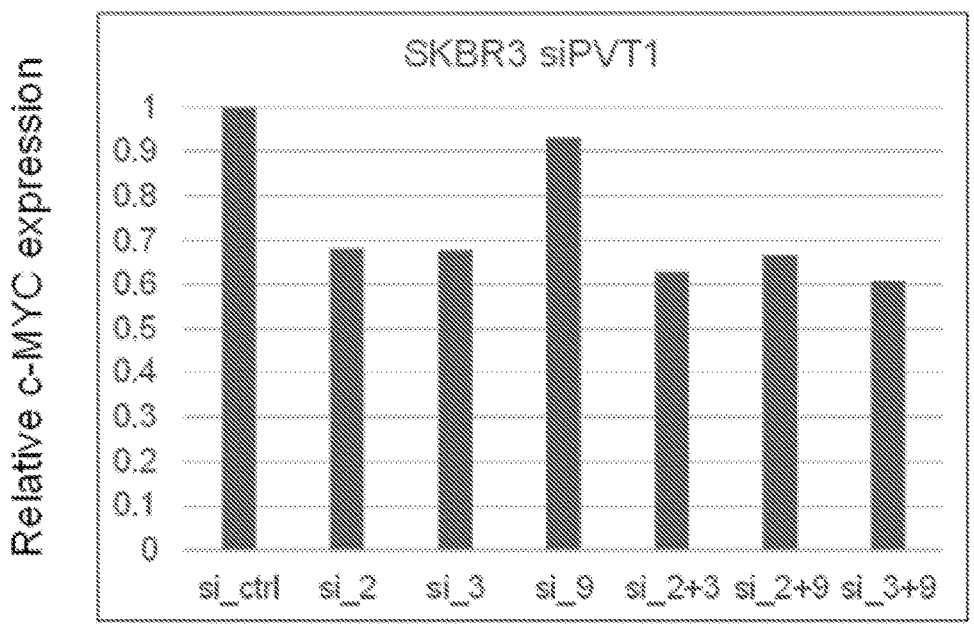

Fig. 9
High vs Low copy number of PVT1/MYC
|  | SKBR3 | NCIH2170 | NCIH1972 | MSTO-211H | COLO-320 | PC-3 | DU145 | U2OS |
|---|---|---|---|---|---|---|---|---|
| PVT1_Copy Number | 2.7844 | 3.5924 | 3.1994 | 3.0149 | 3.4936 | 0.9531 | 0.3192 | 0.7345 |
| MYC_Copy Number | 2.4697 | 3.5924 | 3.1994 | 3.0149 | 3.4936 | 0.9531 | 0.3192 | 0.7345 |
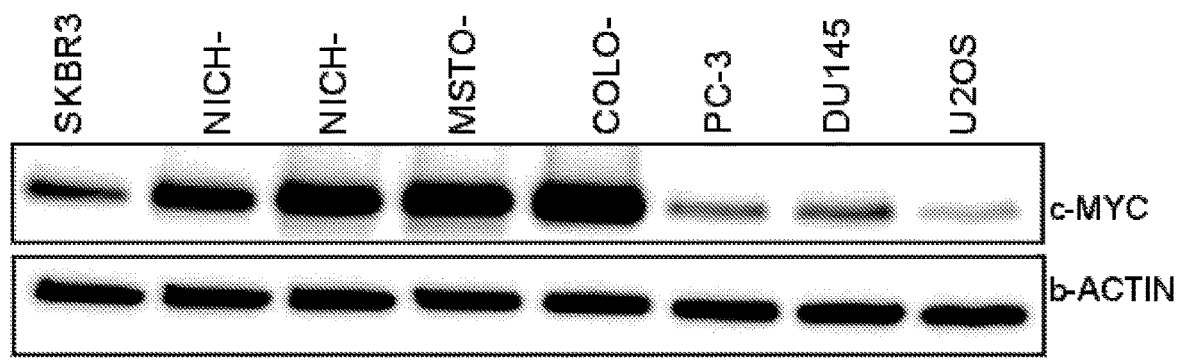
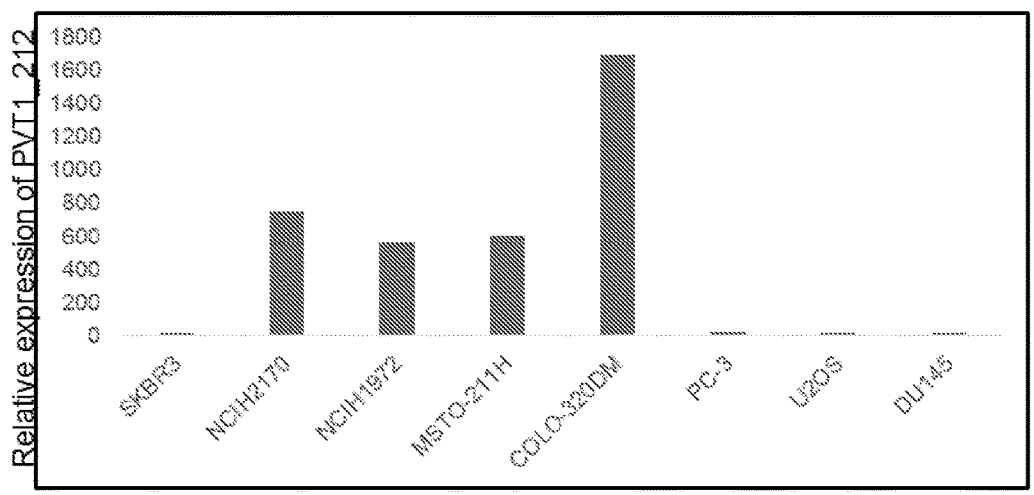

Fig. 10
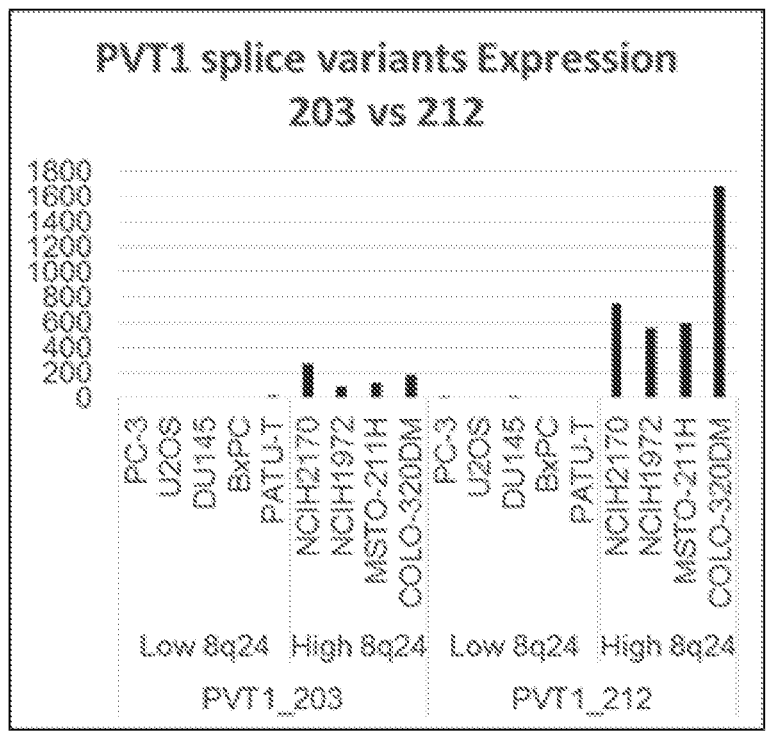
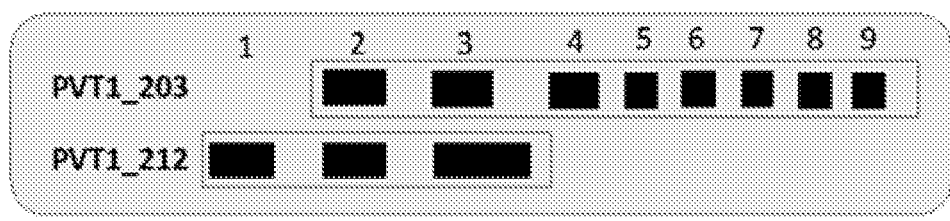
| | | PVT1_Copy Number | MYC_Copy Number |
|---|---|---|---|
| High 8q24 | NCIH2170 | 3.5924 | 3.5924 |
| | NCIH1972 | 3.1994 | 3.1994 |
| | MSTO-211H | 3.0149 | 3.0149 |
| | COLO-320DM | 3.4936 | 3.4936 |
| Low 8q24 | PC-3 | 0.9531 | 0.9531 |
| | U2OS | 0.7345 | 0.7345 |
| | DU145 | 0.3192 | 0.3192 |
| | BxPC | 0.2885 | 0.2885 |
| | PATU-T | 0.6916 | 0.4641 |

Fig. 12C

```
JT1_201-Exon2    GCCTGATCTTTTGGCCAGAAGGAGATTAAAAAGATGCCCCTCAAGATGGCTGTGCCTGTC    60
JT1_205-Exon2    GCCTGATCTTTTGGCCAGAAGGAGATTAAAAAGATGCCCCTCAAGATGGCTGTGCCTGTC    60
JT1_207-Exon2    GCCTGATCTTTTGGCCAGAAGGAGATTAAAAAGATGCCCCTCAAGATGGCTGTGCCTGTC    60
JT1_210-Exon2    GCCTGATCTTTTGGCCAGAAGGAGATTAAAAAGATGCCCCTCAAGATGGCTGTGCCTGTC    60
JT1_212-Exon2    ████████████████████████████████GATGCCCCTCAAGATGGCTGTGCCTGTC    60
JT1_215-Exon2    GCCTGATCTTTTGGCCAGAAGGAGATTAAAAAGATGCCCCTCAAGATGGCTGTGCCTGTC    60
JT1_216-Exon2    GCCTGATCTTTTGGCCAGAAGGAGATTAAAAAGATGCCCCTCAAGATGGCTGTGCCTGTC    60
JT1_219-Exon2    GCCTGATCTTTTGGCCAGAAGGAGATTAAAAAGATGCCCCTCAAGATGGCTGTGCCTGTC    60
JT1_203-Exon2    ---------------------------------------CTCAAGATGGCTGTGCCTGTC    21
JT1_206-Exon2    ------------------------------------------------------------    0
JT1_208-Exon2    ------------------------------------------------------------    0
JT1_209-Exon2    ---------------------------------------------------------GTC    3

JT1_201-Exon2    AGCTGCATGGAGCTTCGTTCAAGTATTTTCTGAGCCTGATGGATTTACAGTGATCTTCAG    120
JT1_205-Exon2    AGCTGCATGGAGCTTCGTTCAAGTATTTTCTGAGCCTGATGGATTTACAGTGATCTTCAG    120
JT1_207-Exon2    AGCTGCATGGAGCTTCGTTCAAGTATTTTCTGAGCCTGATGGATTTACAGTGATCTTCAG    120
JT1_210-Exon2    AGCTGCATGGAGCTTCGTTCAAGTATTTTCTGAGCCTGATGGATTTACAGTGATCTTCAG    120
JT1_212-Exon2    AGCTGCATGGAGCTTCGTTCAAGTATTTTCTGAGCCTGATGGATTTACAGTGATCTTCAG    120
JT1_215-Exon2    AGCTGCATGGAGCTTCGTTCAAGTATTTTCTGAGCCTGATGGATTTACAGTGATCTTCAG    120
JT1_216-Exon2    AGCTGCATGGAGCTTCGTTCAAGTATTTTCTGAGCCTGATGGATTTACAGTGATCTTCAG    120
JT1_219-Exon2    AGCTGCATGGAGCTTCGTTCAAGTATTTTCTGAGCCTGATGGATTTACAGTGATCTTCAG    120
JT1_203-Exon2    AGCTGCATGGAGCTTCGTTCAAGTATTTTCTGAGCCTGATGGATTTACAGTGATCTTCAG    81
JT1_206-Exon2    ------------------------------------------------------------    0
JT1_208-Exon2    ----------------------------TCTGAGCCTGATGGATTTACAGTGATCTTCAG    32
JT1_209-Exon2    AGCTGCATGGAGCTTCGTTCAAGTATTTTCTGAGCCTGATGGATTTACAGTGATCTTCAG    63

JT1_201-Exon2    TGGTCTGGGGAATAACGCTGGTGGAACCATGCACTGGAATGACACACGCCCGGCACATTT    180
JT1_205-Exon2    TGGTCTGGGGAATAACGCTGGTGGAACCATGCACTGGAATGACACACGCCCGGCACATTT    180
JT1_207-Exon2    TGGTCTGGGGAATAACGCTGGTGGAACCATGCACTGGAATGACACACGCCCGGCACATTT    180
JT1_210-Exon2    TGGTCTGGGGAATAACGCTGGTGGAACCATGCA---------------------------    153
JT1_212-Exon2    TGGTCTGGGGAATAACGCTGGTGGAACCATGCACTGGAATGACACACGCCCGGCACATTT    180
JT1_215-Exon2    TGGTCTGGGGAATAACGCTGGTGGAACCATGCACTGGAATGACACACGCCCGGCACATTT    180
JT1_216-Exon2    TGGTCTGGGGAATAACGCTGGTGGAACCATGCACTGGAATGACACACGCCCGGCACATTT    180
JT1_219-Exon2    TGGTCTGGGGAATAACGCTGGTGGAACCATGCACTGGAATGACACACGCCCGGCACATTT    180
JT1_203-Exon2    TGGTCTGGGGAATAACGCTGGTGGAACCATGCACTGGAATGACACACGCCCGGCACATTT    141
JT1_206-Exon2    ------------------------------------------------------------    0
JT1_208-Exon2    TGGTCTGGGGAATAACGCTGGTGGAACCATGCACTGGAATGACACACGCCCGGCACATTT    92
JT1_209-Exon2    TGGTCTGGGGAATAACGCTGGTGGAACCATGCACTGGAATGACACACGCCCGGCACATTT    123

JT1_201-Exon2    CAGGATACTAAAAGTGGTTTTAAGGGAGGCTGTGGCTGAATGCCTCATGGATTCTTACAG    240
JT1_205-Exon2    CAGGATACTAAAAGTGGTTTTAAGGGAGGCTGTGGCTGAATGCCTCATGGATTCTTACAG    240
JT1_207-Exon2    CAGGATACTAAAAGTGGTTTTAAGGGAGGCTGTGGCTGAATGCCTCATGGATTCTTACAG    240
JT1_210-Exon2    ------------------------------------------------------------    153
JT1_212-Exon2    CAGGATACTAAAAGTGGTTTTAAGGGAGGCTGTGGCTGAATGCCTCATGGATTCTTACAG    240
JT1_215-Exon2    CAGGATACTAAAAGTGGTTTTAAGGGA---------------------------------    207
JT1_216-Exon2    CAGGATACTAAAAGTGGTTTTAAGGGAGGCTGTGGCTGAATGCCTCATGGATTCTTACAG    240
JT1_219-Exon2    CAGGATACTAAAAGTGGTTTTAAGGGAGGCTGTGGCTGAATGCCTCATGGATTCTTACAG    240
JT1_203-Exon2    CAGGATACTAAAAGTGGTTTTAAGGGAGGCTGTGGCTGAATGCCTCATGGATTCTTACAG    201
JT1_206-Exon2    ------------------------------------------------------------    0
JT1_208-Exon2    CAGGATACTAAAAGTGGTTTTAAGGGAGGCTGTGGCTGAATGCCTCATGGATTCTTACAG    152
JT1_209-Exon2    CAGGATACTAAAAGTGGTTTTAAGGGAGGCTGTGGCTGAATGCCTCATGGATTCTTACAG    183

JT1_201-Exon2    CTTGGATGTCCATGGGGACGAAGGACTGCAGCTGGCTGAGAGGGTTGAGATCTCTGTTT    300
JT1_205-Exon2    CTTGGATGTCCATGGGGACGAAGGACTGCAGCTGGCTGAGAGGGTTGAGATCTCTGTTT    300
JT1_207-Exon2    CTTGGATGTCCATGGGGACGAAGGACTGCAGCTGGCTGAGAGGGTTGAGATCTCTGTTT    300
JT1_210-Exon2    -----------------------------------------------------------    153
JT1_212-Exon2    CTTGGATGTCCATGGGGACGAAGGACTGCAGCTGGCTGAGAGGGTTGAGATCTCTGTTT    300
JT1_215-Exon2    -----------------------------------------------------------    207
JT1_216-Exon2    CTTGGATGTCCATGGGGACGAAGGACTGCAGCTGGCTGAGAGGGTTGAGATCTCTGTTT    300
JT1_219-Exon2    CTTGGATGTCCATGGGGACGAAGGACTGCAGCTGGCTGAGAGGGTTGAGATCTCTGTTT    300
JT1_203-Exon2    CTTGGATGTCCATGGGGACGAAGGACTGCAGCTGGCTGAGAGGGTTGAGATCTCTGTTT    261
JT1_206-Exon2    ----------------------------------------AGGGTTGAGATCTCTGTTT    19
JT1_208-Exon2    CTTGGATGTCCATGGGGACGAAGGACTGCAGCTGGCTGAGAGGGTTGAGATCTCTGTTT    212
JT1_209-Exon2    CTTGGATGTCCATGGGGACGAAGGACTGCAGCTGGCTGAGAGGGTTGAGATCTCTGTTT    243

JT1_201-Exon2    ACTTAGATCTCTGCCAACTTCCTTTGGGTCTCCCTATGGAATGTAAGACCCCGACTCTTC    360
JT1_205-Exon2    ACTTAGATCTCTGCCAACTTCCTTTGGGTCTCCCTATGGAATGT----------------    344
JT1_207-Exon2    ACTTAGATCTCTGCCAACTTCCTTTGGGTCTCCCTATGGAATGTAAGACCCCGACTCTTC    360
JT1_210-Exon2    ------------------------------------------------------------    153
JT1_212-Exon2    ACTTAGATCTCTGCCAACTTCCTTTGGGTCTCCCTATGGAATGTAAGACCCCGACTCTTC    360
JT1_215-Exon2    ------------------------------------------------------------    207
JT1_216-Exon2    ACTTAGATCTCTGCCAACTTCCTTTGGGTCTCCCTATGGAATGTAAGACCCCGACTCTTC    360
JT1_219-Exon2    ACTTAGATCTCTGCCAACTTCCTTTGGGTCTCCCTATGGAATGTAAGACCCCGACTCTTC    360
JT1_203-Exon2    ACTTAGATCTCTGCCAACTTCCTTTGGGTCTCCCTATGGAATGTAAGACCCCGACTCTTC    321
JT1_206-Exon2    ACTTAGATCTCTGCCAACTTCCTTTGGGTCTCCCTATGGAATGTAAGACCCCGACTCTTC    79
JT1_208-Exon2    ACTTAGATCTCTGCCAACTTCCTTTGGGTCTCCCTATGGAATGTAAGACCCCGACTCTTC    272
JT1_209-Exon2    ACTTAGATCTCTGCCAACTTCCTTTGGGTCTCCCTATGGAATGTAAGACCCCGACTCTTC    303

JT1_201-Exon2    CTGGTGAAGCATCTGATGCACGTTCCA---------------------    387
JT1_205-Exon2    ------------------------------------------------    344
JT1_207-Exon2    CTGGTGAAGCAT------------------------------------    372
JT1_210-Exon2    ------------------------------------------------    153
JT1_212-Exon2    CTGGTGAAGCATCTGATGCAC██████████████████████████    410
JT1_215-Exon2    ------------------------------------------------    207
JT1_216-Exon2    CTGGTGAAGCATCTGATGCACGTTCCATCCGGCGC-------------    395
JT1_219-Exon2    CTGG--------------------------------------------    364
JT1_203-Exon2    CTGGTGAAGCATCTGATGCACGTTCCATCCGGCGCTCAGCTGGGCTTGAG    371
JT1_206-Exon2    CTGGTGAAGCATCTGATGCACGTTCCATCCGGCGCTCAGCTGGGCTTGAG    129
JT1_208-Exon2    CTGGTGAAGCATCTGATGCACGTTCCATCCGGCGCTCAGCTGGGCTTGAG    322
JT1_209-Exon2    CTGGTGAAGCATCTGATGCACGTTCCATCCGGCGCTCAGCTGGGCTTGAG    353
```

Transwell Migration Experiment in U2OS

Similarity in Expression of PVT1_212 and circPVT1 in MB PDX samples

Expression of PVT1_212 and circPVT1
In High and Low Copy Number 8q24 Cell Lines RT-qPCR (Exon1-2)
Medulloblastoma samples from Michael D Taylor, MD, from Hospital for Sick Kids

| | Cq_Ex12 (ave) | Cq_GAPDH (ave) | Δ Ex12 | Exp_Ex12 |
|---|---|---|---|---|
| #1 | 29.625 | 18.865 | 10.76 | 0.000577 |
| #2 | 30.37 | 19.545 | 10.825 | 0.000551 |
| #3 | 26.615 | 20.14 | 6.475 | 0.011242 |
| #4 | 18.49 | 19.71 | -1.22 | 2.329467 |
| #5 | 21.04 | 19.855 | 1.185 | 0.439825 |
| #6 | 25.1 | 19.075 | 6.025 | 0.015357 |
| #7 | 27.485 | 19.28 | 8.205 | 0.003389 |
| #8 | 25.51 | 19.605 | 5.905 | 0.016689 |
| #9 | 26.2 | 19.46 | 6.74 | 0.009355 |
| #10 | 26.985 | 20.87 | 6.115 | 0.014428 |
| #11 | 30.2 | 20.91 | 9.29 | 0.001597 |
| #12 | 24.79 | 19.45 | 5.34 | 0.024689 |
| #13 | 29.21 | 19.41 | 9.8 | 0.001122 |
| #14 | 29.025 | 19.79 | 9.235 | 0.00166 |
| #15 | 29.695 | 20.455 | 9.24 | 0.001654 |
| #23 | 24.366667 | 20.286667 | 4.08 | 0.059129 |
| #1338 | 26.52 | 20.22 | 6.3 | 0.012691 |
| #1377 | 21.416667 | 19.13 | 2.286667 | 0.204946 |
| #2032 | 26.163333 | 19.6 | 6.563333 | 0.010574 |
| #2391 | 24.576667 | 20.4 | 4.176667 | 0.055297 |
| #2494 | 25.5 | 19.406667 | 6.093333 | 0.014646 |
| #2510 | 25.353333 | 20.896667 | 4.456667 | 0.045542 |
| #3183 | 26.486667 | 20.233333 | 6.253333 | 0.013109 |

Fig. 28

Sequence Analysis of Highest Expressing Variant

- Clone M4

Reverse Reads

Exon 1/2 Splice Junction Putative Sequence

Forward Reads

- Clone M5

Reverse Reads

Exon 1/2 Splice Junction Putative Sequence

Forward Reads

Fig. 29

Sequence Analysis of Highest Expressing Variant

- Clone 23

Reverse Reads

Exon 1/2 Splice Junction Putative Sequence

Forward Reads

- Clone 1377

Reverse Reads

Exon 1/2 Splice Junction Putative Sequence

Forward Reads

| Cell line | Cancer type | MYC copy number | PVT1 copy number |
|---|---|---|---|
| PSN-1 | Pancreas | 2.6549 | 2.6549 |
| NCI-H2170 | Lung | 3.5924 | 3.5924 |
| NCI-H1792 | Lung | 3.1994 | 3.1994 |
| MSTO-211H | Pleura (Mesothelioma) | 3.0149 | 3.0149 |
| U2OS | Bone (Osteosarcoma) | 0.7345 | 0.7345 |
| BXPC-3 | Pancreas | 0.2885 | 0.2885 |
| DU 145 | Prostate | 0.3192 | 0.3192 |
| PC-3 | Prostate | 0.9531 | 0.9531 |

SEQUENCE LISTING

<160> NUMBER OF SEQ ID NOS: 95

<210> SEQ ID NO 1
<211> LENGTH: 410
<212> TYPE: DNA
<213> ORGANISM: Homo sapiens

<400> SEQUENCE: 1

```
gcctgatctt ttggccagaa ggagattaaa aagatgcccc tcaagatggc tgtgcctgtc      60
agctgcatgg agcttcgttc aagtattttc tgagcctgat ggatttacag tgatcttcag     120
tggtctgggg aataacgctg gtggaaccat gcactggaat gacacacgcc cggcacattt     180
caggatacta aaagtggttt taagggaggc tgtggctgaa tgcctcatgg attcttacag     240
cttggatgtc catgggggac gaaggactgc agctggctga gagggttgag atctctgttt     300
acttagatct ctgccaactt cctttgggtc tccctatgga atgtaagacc ccgactcttc     360
ctggtgaagc atctgatgca cgttccatcc ggcgctcagc tgggcttgag                410
```

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2

```
ccatccggcg ctcag                                                       15
```

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3

```
ugggcuugag gccugaucuu u                                                21
```

-continued

```
<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
agaucaggcc ucaagcccau u                                              21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gccatcatga tggtacttt                                                 19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
caucaugaug guacuuuaat t                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uuaaaguacc aucaugaugg c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccggcacatt tcaggatact a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 9
ggcacauuuc aggauacuat t                                         21

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uaguauccug amugugccgg                                            20

<210> SEQ ID NO 11
<211> LENGTH: 315
<212> TYPE: DNA
<213> ORGANISM: Homo sapiens

<400> SEQUENCE: 11
atgcacgttc catccggcgc tcagctgggc ttgaggcctg atcttttggc cagaaggaga    60
ttaaaaagat gcccctcaag atggctgtgc ctgtcagctg catggagctt cgttcaagta   120
ttttctgagc ctgatggatt tacagtgatc ttcagtggtc tggggaataa cgctggtgga   180
accatgcact ggaatgacac acgcccggca catttcagga tactaaaagt ggttttaagg   240
gaggctgtgg ctgaatgcct catggattct tacagcttgg atgtccatgg gggacgaagg   300
actgcagctg gctga                                                   315

<210> SEQ ID NO 12
<211> LENGTH: 104
<212> TYPE: PRT
<213> ORGANISM: Homo sapiens

<400> SEQUENCE: 12

Met His Val Pro Ser Gly Ala Gln Leu Gly Leu Arg Pro Asp Leu Leu
1               5                   10                  15

Ala Arg Arg Arg Leu Lys Arg Cys Pro Ser Arg Trp Leu Cys Leu Ser
            20                  25                  30

Ala Ala Trp Ser Phe Val Gln Val Phe Ser Glu Pro Asp Gly Phe Thr
        35                  40                  45

Val Ile Phe Ser Gly Leu Gly Asn Asn Ala Gly Gly Thr Met His Trp
    50                  55                  60

Asn Asp Thr Arg Pro Ala His Phe Arg Ile Leu Lys Val Val Leu Arg
65                  70                  75                  80

Glu Ala Val Ala Glu Cys Leu Met Asp Ser Tyr Ser Leu Asp Val His
                85                  90                  95

Gly Gly Arg Arg Thr Ala Ala Gly
            100

<210> SEQ ID NO 13
<211> LENGTH: 315
<212> TYPE: DNA
<213> ORGANISM: Homo sapiens

<400> SEQUENCE: 13
atgcacgttc catccggcgc tcagctgggc ttgaggcctg atcttttggc cagaaggaga    60
ttaaaaagat gcccctcaag atggctgtgc ctgtcagctg catggagctt cgttcaagta   120
ttttctgagc ctgatggatt tacagtgatc ttcagtggtc tggggaataa cgctggtgga   180

```
accatgcact ggaatgacac acgcccggca catttcagga tactaaaagt ggttttaagg    240
gaggctgtgg ctgaatgcct catggattct tacagcttgg atgtccatgg gggacgaagg    300
actgcagctg gctga                                                    315
```

<210> SEQ ID NO 14
<211> LENGTH: 104
<212> TYPE: PRT
<213> ORGANISM: Homo sapiens

<400> SEQUENCE: 14

```
Met His Val Pro Ser Gly Ala Gln Leu Gly Leu Arg Pro Asp Leu Leu
1               5                   10                  15

Ala Arg Arg Arg Leu Lys Arg Cys Pro Ser Arg Trp Leu Cys Leu Ser
                20                  25                  30

Ala Ala Trp Ser Phe Val Gln Val Phe Ser Glu Pro Asp Gly Phe Thr
            35                  40                  45

Val Ile Phe Ser Gly Leu Gly Asn Asn Ala Gly Gly Thr Met His Trp
        50                  55                  60

Asn Asp Thr Arg Pro Ala His Phe Arg Ile Leu Lys Val Val Leu Arg
65                  70                  75                  80

Glu Ala Val Ala Glu Cys Leu Met Asp Ser Tyr Ser Leu Asp Val His
                85                  90                  95

Gly Gly Arg Arg Thr Ala Ala Gly
            100
```

<210> SEQ ID NO 15
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atgcatgtac cttccggcgc ccaactcggc ctcagaccgg acctgttggc ccgacgacga    60
ctgaagcgat gccctagcag gtggctctgt ctgtcagctg cgtggtcttt tgtccaagtt    120
ttctccgagc cagatggttt cacagttatt ttctccgggt tgggtaacaa tgcgggcggc    180
actatgcatt ggaatgatac tagaccagca cactttagga tcttgaaagt ggtcctcagg    240
gaagcggtgg cggaatgtct gatggatagt tattcactgg acgtacatgg ggtcgccga    300 acagccgcag gctga                                                   315
```

<210> SEQ ID NO 16
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
tgacacgttc catccggcgc tcagctgggc ttgaggcctg atcttttggc cagaaggaga    60
ttaaaaagat gcccctcaag atggctgtgc ctgtcagctg catggagctt cgttcaagta    120
ttttctgagc ctgatggatt tacagtgatc ttcagtggtc tggggaataa cgctggtgga    180
acctgacact ggaatgacac acgcccggca catttcagga tactaaaagt ggttttaagg    240
gaggctgtgg ctgaatgcct ctgagattct tacagcttgg atgtccatgg gggacgaagg    300
```

```
actgcagctg gctga                                                      315
```

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
cggcgctcag ctgggcttga ggcctgatct tttggccaga aggagatt                   48
```

<210> SEQ ID NO 18
<211> LENGTH: 387
<212> TYPE: DNA
<213> ORGANISM: Homo sapiens

<400> SEQUENCE: 18

```
gcctgatctt ttggccagaa ggagattaaa aagatgcccc tcaagatggc tgtgcctgtc      60
agctgcatgg agcttcgttc aagtattttc tgagcctgat ggatttacag tgatcttcag     120
tggtctgggg aataacgctg gtggaaccat gcactggaat gacacacgcc cggcacattt     180
caggatacta aaagtggttt taagggaggc tgtggctgaa tgcctcatgg attcttacag     240
cttggatgtc catggggac gaaggactgc agctggctga gagggttgag atctctgttt     300
acttagatct ctgccaactt cctttgggtc tccctatgga atgtaagacc ccgactcttc     360
ctggtgaagc atctgatgca cgttcca                                        387
```

<210> SEQ ID NO 19
<211> LENGTH: 344
<212> TYPE: DNA
<213> ORGANISM: Homo sapiens

<400> SEQUENCE: 19

```
gcctgatctt ttggccagaa ggagattaaa aagatgcccc tcaagatggc tgtgcctgtc      60
agctgcatgg agcttcgttc aagtattttc tgagcctgat ggatttacag tgatcttcag     120
tggtctgggg aataacgctg gtggaaccat gcactggaat gacacacgcc cggcacattt     180
caggatacta aaagtggttt taagggaggc tgtggctgaa tgcctcatgg attcttacag     240
cttggatgtc catggggac gaaggactgc agctggctga gagggttgag atctctgttt     300
acttagatct ctgccaactt cctttgggtc tccctatgga atgt                     344
```

<210> SEQ ID NO 20
<211> LENGTH: 372
<212> TYPE: DNA
<213> ORGANISM: Homo sapiens

<400> SEQUENCE: 20

```
gcctgatctt ttggccagaa ggagattaaa aagatgcccc tcaagatggc tgtgcctgtc      60
agctgcatgg agcttcgttc aagtattttc tgagcctgat ggatttacag tgatcttcag     120
tggtctgggg aataacgctg gtggaaccat gcactggaat gacacacgcc cggcacattt     180
caggatacta aaagtggttt taagggaggc tgtggctgaa tgcctcatgg attcttacag     240
cttggatgtc catggggac gaaggactgc agctggctga gagggttgag atctctgttt     300
acttagatct ctgccaactt cctttgggtc tccctatgga atgtaagacc ccgactcttc     360
ctggtgaagc at                                                        372
```

```
<210> SEQ ID NO 21
<211> LENGTH: 153
<212> TYPE: DNA
<213> ORGANISM: Homo sapiens

<400> SEQUENCE: 21
gcctgatctt ttggccagaa ggagattaaa aagatgcccc tcaagatggc tgtgcctgtc      60
agctgcatgg agcttcgttc aagtattttc tgagcctgat ggatttacag tgatcttcag     120
tggtctgggg aataacgctg gtggaaccat gca                                   153

<210> SEQ ID NO 22
<211> LENGTH: 410
<212> TYPE: DNA
<213> ORGANISM: Homo sapiens

<400> SEQUENCE: 22
gcctgatctt ttggccagaa ggagattaaa aagatgcccc tcaagatggc tgtgcctgtc      60
agctgcatgg agcttcgttc aagtattttc tgagcctgat ggatttacag tgatcttcag     120
tggtctgggg aataacgctg gtggaaccat gcactggaat gacacacgcc cggcacattt     180
caggatacta aaagtggttt taagggaggc tgtggctgaa tgcctcatgg attcttacag     240
cttggatgtc catggggac gaaggactgc agctggctga gagggttgag atctctgttt      300
acttagatct ctgccaactt cctttgggtc tccctatgga atgtaagacc ccgactcttc     360
ctggtgaagc atctgatgca cgttccatcc ggcgctcagc tgggcttgag                410

<210> SEQ ID NO 23
<211> LENGTH: 207
<212> TYPE: DNA
<213> ORGANISM: Homo sapiens

<400> SEQUENCE: 23
gcctgatctt ttggccagaa ggagattaaa aagatgcccc tcaagatggc tgtgcctgtc      60
agctgcatgg agcttcgttc aagtattttc tgagcctgat ggatttacag tgatcttcag     120
tggtctgggg aataacgctg gtggaaccat gcactggaat gacacacgcc cggcacattt     180
caggatacta aaagtggttt taaggga                                          207

<210> SEQ ID NO 24
<211> LENGTH: 395
<212> TYPE: DNA
<213> ORGANISM: Homo sapiens

<400> SEQUENCE: 24
gcctgatctt ttggccagaa ggagattaaa aagatgcccc tcaagatggc tgtgcctgtc      60
agctgcatgg agcttcgttc aagtattttc tgagcctgat ggatttacag tgatcttcag     120
tggtctgggg aataacgctg gtggaaccat gcactggaat gacacacgcc cggcacattt     180
caggatacta aaagtggttt taagggaggc tgtggctgaa tgcctcatgg attcttacag     240
cttggatgtc catggggac gaaggactgc agctggctga gagggttgag atctctgttt      300
acttagatct ctgccaactt cctttgggtc tccctatgga atgtaagacc ccgactcttc     360
ctggtgaagc atctgatgca cgttccatcc ggcgc                                 395

<210> SEQ ID NO 25
<211> LENGTH: 364
<212> TYPE: DNA
```

<213> ORGANISM: Homo sapiens

<400> SEQUENCE: 25

```
gcctgatctt ttggccagaa ggagattaaa aagatgcccc tcaagatggc tgtgcctgtc    60
agctgcatgg agcttcgttc aagtattttc tgagcctgat ggatttacag tgatcttcag   120
tggtctgggg aataacgctg gtggaaccat gcactggaat gacacacgcc cggcacattt   180
caggatacta aaagtggttt taagggaggc tgtggctgaa tgcctcatgg attcttacag   240
cttggatgtc catgggggac gaaggactgc agctggctga gagggttgag atctctgttt   300
acttagatct ctgccaactt cctttgggtc tccctatgga atgtaagacc ccgactcttc   360
ctgg                                                                364
```

<210> SEQ ID NO 26
<211> LENGTH: 371
<212> TYPE: DNA
<213> ORGANISM: Homo sapiens

<400> SEQUENCE: 26

```
ctcaagatgg ctgtgcctgt cagctgcatg gagcttcgtt caagtatttt ctgagcctga    60
tggatttaca gtgatcttca gtggtctggg gaataacgct ggtggaacca tgcactggaa   120
tgacacacgc ccggcacatt tcaggatact aaaagtggtt ttaagggagg ctgtggctga   180
atgcctcatg gattcttaca gcttggatgt ccatggggga cgaaggactg cagctggctg   240
agagggttga gatctctgtt tacttagatc tctgccaact tcctttgggt ctccctatgg   300
aatgtaagac cccgactctt cctggtgaag catctgatgc acgttccatc cggcgctcag   360
ctgggcttga g                                                        371
```

<210> SEQ ID NO 27
<211> LENGTH: 129
<212> TYPE: DNA
<213> ORGANISM: Homo sapiens

<400> SEQUENCE: 27

```
agggttgaga tctctgttta cttagatctc tgccaacttc ctttgggtct ccctatggaa    60
tgtaagaccc cgactcttcc tggtgaagca tctgatgcac gttccatccg gcgctcagct   120
gggcttgag                                                           129
```

<210> SEQ ID NO 28
<211> LENGTH: 322
<212> TYPE: DNA
<213> ORGANISM: Homo sapiens

<400> SEQUENCE: 28

```
tctgagcctg atggatttac agtgatcttc agtggtctgg ggaataacgc tggtggaacc    60
atgcactgga atgacacacg cccggcacat ttcaggatac taaaagtggt tttaagggag   120
gctgtggctg aatgcctcat ggattcttac agcttggatg tccatggggg acgaaggact   180
gcagctggct gagagggttg agatctctgt ttacttagat ctctgccaac ttcctttggg   240
tctccctatg gaatgtaaga ccccgactct tcctggtgaa gcatctgatg cacgttccat   300
ccggcgctca gctgggcttg ag                                            322
```

<210> SEQ ID NO 29
<211> LENGTH: 353
<212> TYPE: DNA

<400> SEQUENCE: 29

```
gtcagctgca tggagcttcg ttcaagtatt ttctgagcct gatggattta cagtgatctt    60
cagtggtctg gggaataacg ctggtggaac catgcactgg aatgacacac gcccggcaca   120
tttcaggata ctaaaagtgg ttttaaggga ggctgtggct gaatgcctca tggattctta   180
cagcttggat gtccatgggg gacgaaggac tgcagctggc tgagagggtt gagatctctg   240
tttacttaga tctctgccaa cttcctttgg gtctccctat ggaatgtaag accccgactc   300
ttcctggtga agcatctgat gcacgttcca tccggcgctc agctgggctt gag          353
```

<210> SEQ ID NO 30
<211> LENGTH: 10
<212> TYPE: DNA
<213> ORGANISM: Homo sapiens

<400> SEQUENCE: 30

```
cctgatcttt                                                            10
```

<210> SEQ ID NO 31
<211> LENGTH: 10
<212> TYPE: DNA
<213> ORGANISM: Homo sapiens

<400> SEQUENCE: 31

```
gggcttgagg                                                            10
```

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

```
gctgggcttg aggcctgatc ttttg                                           25
```

<210> SEQ ID NO 33
<211> LENGTH: 104
<212> TYPE: PRT
<213> ORGANISM: Homo sapiens

<400> SEQUENCE: 33

```
Met His Val Pro Ser Gly Ala Gln Leu Gly Leu Arg Pro Asp Leu Leu
1               5                   10                  15

Ala Arg Arg Arg Leu Lys Arg Cys Pro Ser Arg Trp Leu Cys Leu Ser
                20                  25                  30

Ala Ala Trp Ser Phe Val Gln Val Phe Ser Glu Pro Asp Gly Phe Thr
            35                  40                  45

Val Ile Phe Ser Gly Leu Gly Asn Asn Ala Gly Gly Thr Met His Trp
        50                  55                  60

Asn Asp Thr Arg Pro Ala His Phe Arg Ile Leu Lys Val Val Leu Arg
65                  70                  75                  80

Glu Ala Val Ala Glu Cys Leu Met Asp Ser Tyr Ser Leu Asp Val His
                85                  90                  95

Gly Gly Arg Arg Thr Ala Ala Gly
            100
```

<210> SEQ ID NO 34

<211> LENGTH: 149
<212> TYPE: PRT
<213> ORGANISM: Homo sapiens

<400> SEQUENCE: 34

```
Met Gly Pro Arg Ala Gly Arg Ala Arg Gly Gly Arg Asp Glu Glu Gly
1               5                   10                  15
Arg Arg Arg Ala Ala Ser Lys Asp Val Pro Arg Asp Pro Arg His Leu
                20                  25                  30
Pro Val Asp Phe Leu Ala Glu Arg Met Leu Ala Val Pro Val Thr Cys
            35                  40                  45
Gly Asp Thr Ala Arg Ser Ala Leu Gln Pro Asp Leu Leu Ala Arg Arg
    50                  55                  60
Arg Leu Lys Arg Cys Pro Ser Arg Trp Leu Cys Leu Ser Ala Ala Trp
65              70                  75                  80
Ser Phe Val Gln Val Phe Ser Glu Pro Asp Gly Phe Thr Val Ile Phe
                85                  90                  95
Ser Gly Leu Gly Asn Asn Ala Gly Gly Thr Met His Trp Asn Asp Thr
            100                 105                 110
Arg Pro Ala His Phe Arg Ile Leu Lys Val Val Leu Arg Glu Ala Val
        115                 120                 125
Ala Glu Cys Leu Met Asp Ser Tyr Ser Leu Asp Val His Gly Gly Arg
    130                 135                 140
Arg Thr Ala Ala Gly
145
```

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
cctgtgacct gtggagacac            20

<210> SEQ ID NO 36
<211> LENGTH: 140
<212> TYPE: DNA
<213> ORGANISM: Homo sapiens

<400> SEQUENCE: 36
cttgcggaaa ggatgttggc ggtccctgtg acctgtggag acacggccag atctgccctc    60
cagcctgatc ttttggccag aaggagatta aaaagatgcc cctcaagatg gctgtgcctg   120
tcagctgcat ggagcttcgt                                               140

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gccatcttga ggggcatctt            20

<210> SEQ ID NO 38
<211> LENGTH: 165

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
aatacgactc actatagggc gaattgaatt tagcggccgc gaattcgccc ttcctgtgac      60
ctgtggagac acggccagat ctgccctcca gcctgatctt ttggccagaa ggagattaaa    120
aagatgcccc tcaagatggc aagggcgaat tcgtttaaac ctgca                    165

<210> SEQ ID NO 39
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
aatacgactc actatagggc gaattgaatt tagcggccgc gaattcgccc ttcctgtgac      60
ctgtggagac acggccagat ctgccctcca gcctgatctt ttggccagaa ggagattaaa    120
aagatgcccc tcaagatggc                                                140

<210> SEQ ID NO 40
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
aatacgactc actatagggc gaattgaatt tagcggccgc gaattcgccc ttcctgtgac      60
ctgtggagac acggccagat ctgccctcca gcctgatctt ttggccagaa ggagattaaa    120
aagatgcccc tcaagatggc                                                140

<210> SEQ ID NO 41
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
aatacgactc actatagggc gaattgaatt tagcggccgc gaattcgccc ttcctgtgac      60
ctgtggagac acggccagat ctgccctcca gcctgatctt ttggccagaa ggagattaaa    120
aagatgcccc tcaagatggc aagggcgaat tcgtttaaac ctgca                    165

<210> SEQ ID NO 42
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
aatacgactc actatagggc gaattgaatt tagcggccgc gaattcgccc ttcctgtgac      60
ctgtggagac acggccagat ctgccctcca gcctgatctt ttggccagaa ggagattaaa    120
```

```
aagatgcccc tcaagatggc                                              140

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aatacgactc actatagg                                                 18

<210> SEQ ID NO 44
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
aatacgactc actatagggc gaattgaatt tagcggccgc gaattcgccc ttcctgtgac    60
ctgtggagac acggccagat ctgccctcca gcctgatctt ttggccagaa ggagattaaa   120
aagatgcccc tcaagatggc aagggcgaat tcgtttaaac ctgca                   165

<210> SEQ ID NO 45
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cctgtgacct gtggagacac ggccagatct gccctccagc tgatctttt ggccagaagg    60 agattaaaaa gatgcccctc aagatggc                                      88

<210> SEQ ID NO 46
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
tagcggccgc gaattcgccc ttcctgtgac ctgtggagac acggccagat ctgccctcca    60
gcctgatctt ttggccagaa ggagattaaa aagatgcccc tcaagatggc aagggcgaat   120
tcgtttaaac ctgca                                                   135

<210> SEQ ID NO 47
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
tagcggccgc gaattcgccc ttcctgtgac ctgtggagac acggccagat ctgccctcca    60
gcctgatctt ttggccagaa ggagattaaa aagatgcccc tcaagatggc aagggcgaat   120
```
tcgtttaaac ctgca                                                        135

<210> SEQ ID NO 48
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gcggccgcga attcgccctt cctgtgacct gtggagacac ggccagatct gccctccagc       60
ctgatctttt ggccagaagg agattaaaaa gatgcccctc aagatggcaa gggcgaattc      120
gtttaaacct gca                                                         133

<210> SEQ ID NO 49
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gccctccagc ctgatctttt ggccagaagg agattaaaaa gatgcccctc aagatggcaa       60
gggcgaattc gtttaaacct gca                                               83

<210> SEQ ID NO 50
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cttttggcca gaaggagatt aaaaagatgc ccctcaagat ggcaagggcg aattcgttta       60
aacctgca                                                                68

<210> SEQ ID NO 51
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tttggccaga aggagattaa aaagatgccc ctcaagatgg caagggcgaa ttcgtttaaa       60
cctgca                                                                  66

<210> SEQ ID NO 52
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttggccaga aggagattaa aaagatgccc ctcaagatgg caagggcgaa ttcgtttaaa       60
cctgca                                                                  66

<210> SEQ ID NO 53
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
tttagcggcc gcgaattcgc ccttcctgtg acctgtggag acacggccag atctgccctc      60
cagcctgatc ttttggccag aaggagatta aaaagatgcc cctcaagatg gcaagggcga     120
attcgtttaa acctgca                                                    137

<210> SEQ ID NO 54
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
tttagcggcc gcgaattcgc ccttcctgtg acctgtggag acacggccag atctgccctc      60
cagcctgatc ttttggccag aaggagatta aaaagatgcc cctcaagatg gcaagggcga     120
attcgtttaa acctgca                                                    137

<210> SEQ ID NO 55
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
tttagcggcc gcgaattcgc ccttcctgtg acctgtggag acacggccag atctgccctc      60
cagcctgatc ttttggccag aaagagatta aaaagatgcc cctcaagatg gcaagggcga     120
attcgtttaa acctgca                                                    137

<210> SEQ ID NO 56
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
tttagcggcc gcgaattcgc ccttcctgtg acctgtggag acacggccag atctgccctc      60
cagcctgatc ttttggccag aaggagatta aaaagatgcc cctcaagatg gcaagggcga     120
attcgtttaa acctgca                                                    137

<210> SEQ ID NO 57
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgca                                                  137

<210> SEQ ID NO 58
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgca                                                  137

<210> SEQ ID NO 59
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgca                                                  137

<210> SEQ ID NO 60
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cctgtgacct gtggagacac ggccagatct gccctccagc ctgatctttt ggccagaagg    60
agattaaaaa gatgcccctc aagatggc                                       88

<210> SEQ ID NO 61
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
tttagcggcc gcgaattcgc ccttcctgtg acctgtggag acacggccag atctgccctc    60
cagcctgatc ttttggccag aaagagatta aaaagatgcc cctcaagatg gcaagggcga   120
attcgtttaa acctgca                                                  137

<210> SEQ ID NO 62
<211> LENGTH: 137
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 62
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgca                                                 137

<210> SEQ ID NO 63
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgca                                                 137

<210> SEQ ID NO 64
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
ttagcggccg cgaattcgcc cttcctgtga cctgtggaga cacggccaga tctgccctcc    60
agcctgatct ttttggccaga aggagattaa aaagatgccc ctcaagatgg caagggcgaa   120
ttcgtttaaa cctgca                                                  136

<210> SEQ ID NO 65
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gcggccgcga attcgccctt cctgtgacct gtggagacac ggccagatct gccctccagc    60
ctgatctttt ggccagaagg agattaaaaa gatgcccctc aagatggcaa gggcgaattc   120
gtttaaacct gca                                                    133

<210> SEQ ID NO 66
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gcggccgcga attcgccctt cctgtgacct gtggagacac ggccagatct gccctccagc    60
ctgatctttt ggccagaagg agattaaaaa gatgcccctc aagatggcaa gggcgaattc   120
gtttaaacct gca                                                    133

<210> SEQ ID NO 67
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
ttggccagaa ggagattaaa aagatgcccc tcaagatggc aagggcgaat tcgtttaaac    60
ctgca    65

<210> SEQ ID NO 68
<211> LENGTH: 135
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg    135

<210> SEQ ID NO 69
<211> LENGTH: 135
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg    135

<210> SEQ ID NO 70
<211> LENGTH: 135
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg    135

<210> SEQ ID NO 71
<211> LENGTH: 112
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71
tttagcggcc gcgaattcgc ccttcctgtg acctgtggag acacggccag atctgccctc    60
cagcctgatc ttttggccag aaggagatta aaaagatgcc cctcaagatg gc            112

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tttagcggcc gcgaattcgc ccttcctgtg acctgtggag acacggcc                 48

<210> SEQ ID NO 73
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg                                                    135

<210> SEQ ID NO 74
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cctgtgacct gtggagacac ggccagatct gccctccagc ctgatctttt ggccagaagg    60
agattaaaaa gatgcccctc aagatggc                                      88

<210> SEQ ID NO 75
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg                                                    135

<210> SEQ ID NO 76
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
tttagcggcc gcgaattcgc ccttcctgtg acctgtggag acacggccag atctgccctc    60
cagcctgatc ttttggccag aaggagatta aaaagatgcc cctcaagatg gcaagggcga   120

```
attcgtttaa acctg                                                    135

<210> SEQ ID NO 77
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg                                                    135

<210> SEQ ID NO 78
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
tagcggccgc gaattcgccc ttcctgtgac ctgtggagac acggcagat ctgccctcca     60 gcctgatctt ttggccagaa ggagattaaa agatgcccc tcaagatggc aagggcgaat   120
tcgtttaaac ctg                                                      133

<210> SEQ ID NO 79
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cttttggcca gaaggagatt aaaaagatgc ccctcaagat ggcaagggcg aattcgttta    60
aacctg                                                              66

<210> SEQ ID NO 80
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ggccagaagg agattaaaaa gatgcccctc aagatggcaa gggcgaattc gtttaaacct    60
g                                                                   61

<210> SEQ ID NO 81
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
tttagcggcc gcgaattcgc ccttcctgtg acctgtggag acacggccag atctgccctc    60
```
cagcctgatc ttttggccag aaggagatta aaaagatgcc cctcaagat          109

<210> SEQ ID NO 82
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                   136

<210> SEQ ID NO 83
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                   136

<210> SEQ ID NO 84
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                   136

<210> SEQ ID NO 85
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                   136

<210> SEQ ID NO 86
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
tttagcggcc gcgaattcgc ccttcctgtg acctgtggag acacggccag atctgccctc    60
cagcctgatc ttttggccag aaggagatta aaaagatgcc cctcaagat              109

<210> SEQ ID NO 87
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                  136

<210> SEQ ID NO 88
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cctgtgacct gtggagacac ggccagatct gccctccagc ctgatctttt ggccagaagg    60
agattaaaaa gatgcccctc aagatggc                                      88

<210> SEQ ID NO 89
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                  136

<210> SEQ ID NO 90
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                  136

<210> SEQ ID NO 91
<211> LENGTH: 136
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                    136

<210> SEQ ID NO 92
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
tagcggccgc gaattcgccc ttcctgtgac ctgtggagac acggccagat ctgccctcca    60
gcctgatctt ttggccagaa ggagattaaa aagatgcccc tcaagatggc aagggcgaat   120
tcgtttaaac ctgc                                                      134

<210> SEQ ID NO 93
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
agcggccgcg aattcgccct tcctgtgacc tgtggagaca cggccagatc tgccctccag    60
cctgatcttt tggccagaag gagattaaaa agatgcccct caagatggca agggcgaatt   120
cgtttaaacc tgc                                                       133

<210> SEQ ID NO 94
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ctgccctcca gcctgatctt ttggccagaa ggagattaaa aagatgcccc tcaagatggc    60
aagggcgaat tcgtttaaac ctgc                                            84

<210> SEQ ID NO 95
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cttttggcca gaaggagatt aaaaagatgc ccctcaagat ggcaagggcg aattcgttta    60
aacctgc                                                               67

ROLE OF PVT1 IN THE DIAGNOSIS AND TREATMENT OF MYC-DRIVEN CANCER

CROSS-REFERENCE TO RELATED APPLICATIONS

This application is a U.S. national stage application of PCT/US2019/031349, filed May 8, 2019, which claims the benefit of U.S. Provisional Application No. 62/668,638, filed May 8, 2018, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 14, 2019, is named 42256-733_601_SEQ.txt and is 38,624 bytes in size.

STATEMENT AS TO FEDERALLY SPONSORED RESEARCH

This invention was made with government support under W81XWH-17-1-0461 awarded by the Medical Research and Development Command, and R01 CA200643 awarded by the National Institutes of Health. The government has certain rights in the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

BACKGROUND OF THE DISCLOSURE

There is a need to for improved diagnosis and therapeutic targeting of MYC-driven cancers.

SUMMARY OF THE DISCLOSURE

The instant disclosure is based on the observation that PVT1 splice variants are related to c-MYC driven cancers, and further in-depth characterization of the PVT1 splice variants revealed insightful components for therapeutic and diagnostic use.

One embodiment provides a method of identifying a subject as having a MYC-driven cancer, comprising: detecting a presence of a PVT1 splice variant or a peptide encoded by the PVT1 splice variant (PEP) in a biological sample isolated from said subject, and identifying said subject as having a MYC-driven cancer based on the presence of the PVT1 splice variant or the PEP, wherein the PVT1 splice variant comprises PVT1_212. In some embodiments, the method further comprises measuring the expression level of a circular PVT1_212 RNA, PVT1_212 splice variant, or PEP, or both, in the biological sample. In some embodiments, the method further comprises measuring the expression level of c-Myc or MYC, or both, in the biological sample.

In some embodiments, the PEP is a PEPc.

In some embodiments, the PEPc comprises 104 amino acids. In some embodiments, the method comprises measuring the expression level of the PEPc in the biological sample. In some embodiments, the biological sample is a liquid sample. In some embodiments, the liquid sample comprises blood or plasma. In some embodiments, the PEPc comprises a liquid biopsy biomarker for identifying if said subject has a MYC-driven cancer.

In some embodiments, the PEP comprises $PEP_L$. In some embodiments, $PEP_L$ comprises 149 amino acids. In some embodiments, the presence or expression levels of the PEP are measured using an antibody against PEPc, an antibody against $PEP_L$, or both.

In some embodiments, the method comprises identifying said subject as having a MYC-driven 8q24 gain cancer. This is determined, in some cases, by the presence of the PVT1_212 splice variant or increased expression level of the PVT_212 splice variant, or the PEP (PEPc or $PEP_L$) relative to reference values. In some embodiments, the method comprises identifying said subject as having a MYC-driven 8q24 gain medulloblastoma, based on an expression level of the PVT1_212 splice variant in the biological sample, wherein the biological sample is a tumor sample isolated from said subject.

In some embodiments, the method further comprises stratifying said subject as a subgroup 3, subgroup 4, Wnt, or Shh type medulloblastoma, based on the expression level of the PVT1_212 splice variant in the tumor sample.

In some embodiments, said subject is stratified as having a subgroup 3 type medulloblastoma if PVT1_212 splice variant expression level is 200 to 1000 fold elevated compared to a reference value. In some embodiments, said subject is stratified as having a subgroup 3, Wnt, or Shh type medulloblastoma if PVT1_212 splice variant expression level is 15 to 200 fold elevated compared to a reference value.

In some embodiments, said subject is stratified as having a subgroup 4 type medulloblastoma if PVT1_212 splice variant expression level is 0 to 15 fold elevated compared to a reference value.

In some embodiments, said subject is identified as having a MYC-driven 8q24 gain medulloblastoma if PVT1_212 splice variant expression level is 200 to 1000 fold elevated compared to a reference value. In some embodiments, the method comprises identifying said subject as having a MYC-driven 8q24 gain cancer, based on an expression level of the PVT1_212 splice variant in the biological sample, wherein the biological sample comprises a tumor sample isolated from said subject. In some embodiments, said subject is identified as having a MYC-driven 8q24 gain cancer if the expression level of the PVT1_212 splice variant is 200 to 1000 fold elevated compared to a reference value. In some embodiments, the reference value comprises expression level of the PVT1_212 splice variant in a biological sample isolated from a subject who does not have a cancer. In some embodiments, the biological sample comprises a tumor sample isolated from said subject and wherein the reference value comprises expression level of the PVT1_212 splice variant in a non-tumor sample from said subject.

One embodiment provides a method of treating cancer in a subject, comprising administering an agent that inhibits a PVT1 splice variant or a peptide encoded by the PVT1 splice variant (PEP), wherein said subject has been identified as having a MYC-driven cancer according to the method of any one of above embodiments.

One embodiment provides a method for selecting a therapy for treating a subject who has a cancer characterized by gain of c-myc, the method comprising (i) detecting a presence of a PVT1 splice variant or a peptide encoded by the PVT1 splice variant (PEP) in a biological sample isolated from said subject, wherein the PVT1 splice variant comprises PVT1_212; and (ii) selecting a therapy comprising an agent that inhibits the PEP for treating said cancer in said subject, if the PVT1 splice variant or the PEP is detected in step (i). In some embodiments, said subject has previously identified as having a cancer characterized by a co-gain of PVT1 and c-Myc. In some embodiments, the co-gain is identified by assaying the copy numbers of PVT1 and c-Myc in the same or a distinct biological sample isolated from said subject and comparing the copy numbers to reference values. In some embodiments, the reference values are copy numbers of PVT1 and c-Myc in a biological sample isolated from a subject who does not have a cancer. In some embodiments, the same or distinct biological sample comprises a tumor sample isolated from said subject and wherein the reference values are copy numbers of PVT1 and c-Myc in a non-tumor sample isolated from said subject. In some embodiments, the co-gain is identified by assaying the copy numbers of PVT1 and c-Myc in the same or a distinct biological sample and comparing with copy numbers of said genes available from the TCGA or ENSEMBL database. In some embodiments, step (i) comprises detecting the presence of the PEP using an anti-PEP antibody, a chromosomal probe specific for the 8q24 locus, or a combination of both. In some embodiments, step (i) comprises measuring the expression level of c-Myc in the biological sample before and after the biological sample is treated with an agent that is specific for exon 3 of the PVT1_212 splice variant, and wherein a reduced expression of c-Myc after treatment of the sample with the agent is indicative of the presence of the PVT1_212 splice variant. In some embodiments, the cancer comprises a 8q24.21 gain cancer. In some embodiments, the cancer comprises medulloblastoma, breast cancer, ovarian cancer, lung cancer, prostate cancer, or a colorectal cancer. In some embodiments, the same or distinct biological sample comprises a biological fluid sample. In some embodiments, the same or distinct biological sample comprises a tumor sample. In some embodiments, the tumor sample comprises a tissue biopsy or a resection.

One embodiment provides a method for characterizing a cancer in a subject, the method comprising: determining a gene expression level of a PVT1 splice variant PVT1_212 in a biological sample isolated from said subject, and characterizing the cancer as a MYC-driven cancer if expression levels of the PVT1_212 is higher than a reference value.

One embodiment provides a method for characterizing a cancer in a subject, the method comprising: detecting a presence of a PVT1 splice variant PVT1_212 in a biological sample isolated from said subject, and characterizing the cancer as a MYC-driven cancer if the PVT1 splice variant is detected in the biological sample.

One embodiment provides a method of treating a cancer in a subject, the method comprising: detecting a presence of a PVT1 splice variant PVT1_212 in a biological sample isolated from said subject, and administering a therapy targeting a peptide encoded by the PVT1_212, wherein said peptide comprises PEPc or PEP$_L$. In some embodiments, said subject has previously identified as having a cancer characterized by a co-gain of PVT1 and c-Myc. In some embodiments, the co-gain is identified by assaying copy numbers of PVT1 and c-Myc in the same or a distinct biological sample isolated from said subject and comparing the copy numbers to reference values. In some embodiments, the reference values are the copy numbers of PVT1 and c-Myc in a biological sample isolated from a subject who does not have a cancer. In some embodiments, the reference values are the copy numbers of PVT1 and c-Myc in a non-tumor sample isolated from said subject. In some embodiments, the co-gain is identified by assaying the copy numbers of PVT1 and c-Myc in the same or a distinct tumor sample isolated from said subject and comparing with copy numbers of said genes available from the TCGA or ENSEMBL database. In some embodiments, the cancer comprises a 8q24.21 gain cancer. In some embodiments, the cancer comprises medulloblastoma, breast cancer, ovarian cancer, lung cancer, prostate cancer, or a colorectal cancer.

One embodiment provides a method of treating a cancer in a subject, the method comprising administering a therapy targeting a peptide encoded by a PVT1 splice variant PVT1_212, wherein the subject has previously been identified as having a cancer characterized by co-gain of PVT1 and c-Myc, wherein said peptide comprises PEPc or PEP$_L$. In some embodiments, the co-gain is identified by assaying copy numbers of PVT1 and c-Myc in a biological sample isolated from said subject and comparing the copy numbers to reference values. In some embodiments, the reference values are the copy numbers of PVT1 and c-Myc in a biological sample isolated from a subject who does not have a cancer. In some embodiments, the reference values are the copy numbers of PVT1 and c-Myc in a non-tumor sample isolated from said subject. In some embodiments, the co-gain is identified by assaying copy numbers of PVT1 and c-Myc in a tumor sample isolated from said subject and comparing with copy numbers of said genes available from the TCGA or ENSEMBL database. In some embodiments, the cancer comprises a 8q24.21 gain cancer. In some embodiments, the cancer comprises medulloblastoma, breast cancer, ovarian cancer, lung cancer, prostate cancer, or a colorectal cancer.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which.

FIG. 4 shows representative data of exemplary splice variant expression in MB PDX samples.

FIG. 5 shows representative data of exemplary PVT_212 expression in MB PDX.

FIG. 6 shows representative data of exemplary expression of PVT1_212 in MB PDX samples.

FIG. 8 shows representative data indicating the effect of siRNAs against PVT1 exons in SKBR3 cells.

FIG. 9 shows representative data of exemplary c-Myc expression in PVT1/MYC high and low copy number cells.

FIG. 10 shows representative data depicting expression of PVT1 splice variants PVT1_212 and PVT1_203.

FIG. 12C indicates junction sequence of the CircPVT1 emanating from the 3' and 5' ends of PVT1_212 (SEQ ID NO.: 22) (highlighted).

FIG. 28 shows sequence analysis of highest expression variants (For Clone M4, SEQ ID NOS 38-52, from line 1 to line 15, respectively; for Clone M5, SEQ ID NOs: 53 to 67, from line 1 to line 15, respectively).

FIG. 29 shows sequence analysis of highest expression variants (For Clone 23, SEQ ID NOS 68-80, from line 1 to line 13, respectively; for Clone 1377, SEQ ID NOs: 81 to 95, from line 1 to line 15, respectively).

DETAILED DESCRIPTION

Figure 1:
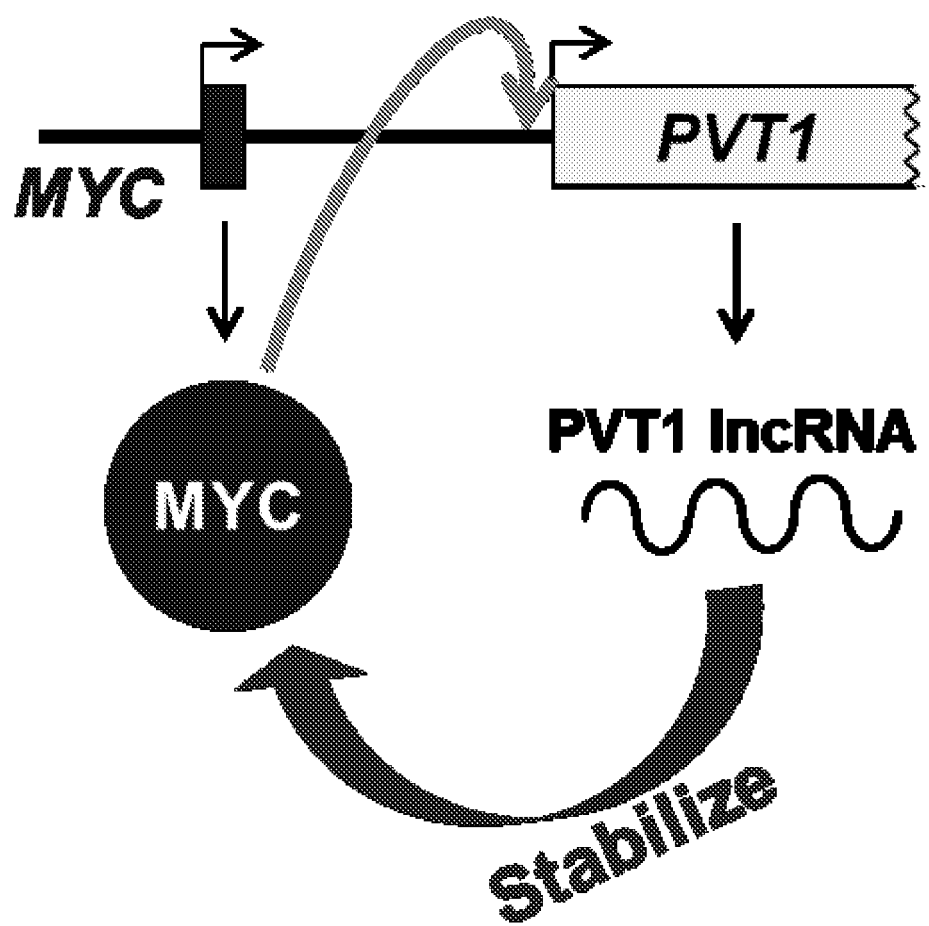
FIG. 1 is a graphical illustration showing the role of PVT1 in MYC augmentation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The term "gene," as used herein, refers to a segment of nucleic acid that encodes an individual protein or RNA (also referred to as a "coding sequence" or "coding region"), optionally together with associated regulatory regions such as promoters, operators, terminators and the like, which may be located upstream or downstream of the coding sequence.

The terms "treat," "treating," and "treatment" is meant to include alleviating or abrogating a disorder, disease, or condition; or one or more of the symptoms associated with the disorder, disease, or condition; or alleviating or eradicating the cause(s) of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "MYC-driven cancer," refers to a cancer characterized by aberrant (typically augmented expression) expression of the c-Myc gene or the MYC protein.

Methods of Diagnosis and Treatment

PVT1, a 'long non-coding RNA' adjacent to prominent oncogene c-Myc, has been shown to co-operate with c-Myc by stabilizing its protein product (MYC) in 8q24 gain cancers (Tseng et al. Nature 512, 82-86, 2014, the correlation is illustrated in FIG. 1). The present disclosure identifies that targeting PVT1 in 8q24 gain cancers provides a therapeutic window to target MYC, an otherwise notoriously undruggable candidate in cancers. Provided herein in one embodiment are methods of identifying a subject as having a MYC-driven cancer by identifying a PVT1 splice variant in a biological sample isolated from the subject. The PVT1 splice variant comprises PVT1_212, in certain embodiments. The method further comprises identifying a cancer subtype in a subject by detecting a presence or expression level of the PVT1_212 splice variant in a biological sample, such as a liquid sample, a tumor sample, or a non-tumor sample. In some embodiments, c-Myc gene expression level is measured in the biological sample along with detection/measurement of PVT1_212 presence or expression levels. In another embodiment, the copy number of PVT1_212, either alone or in combination with the copy number of c-Myc gene, is identified to diagnose a 8q24 gain MYC-driven cancer. Various methods can be used to identify the PVT1_212 splice variant, such as antibody-based detection, quantitative PCR. Upon detection of the PVT1_212 in the biological sample and assaying its expression level, it is possible to identify the cancer as a MYC-driven cancer. In some embodiments, the cancer is medulloblastoma, and the method disclosed herein enables stratification of the medulloblastoma as Subgroup 3, Subgroup 4, Wnt, or Shh type medulloblastoma based on the expression level of the PVT1_212 splice variant, particularly, the elevated expression level compared to reference values. The reference values are, for instance, in biological samples isolated from a subject who does not have cancer, or a non-tumor sample from the same subject whose tumor sample has elevated PVT1_212. In some embodiments, the expression level of PVT1_212 splice variant is elevated greater than about 2-fold, or about 3-fold, or about 4-fold, or about 5-fold, or about 6-fold, or about 7-fold, or about 8-fold, or about 9-fold, or about 10-fold, or about 11-fold, or about 12-fold, or about 13-fold, or about 14-fold, or about 15-fold, or about 16-fold, or about 17-fold, or about 18-fold, or about 19-fold, or about 20 fold or more compared to a reference value.

It is also identified herein that PVT1_212 undergoes backsplicing and form a circular RNA (CircPVT1_212). Since circular RNAs are more stable than linear RNAs due to their resistance to exonucleases, and can be identified in blood/plasma derived patient samples, this disclosure identifies that, in some cases, the CircPVT1_212 is used as a liquid biopsy marker for MYC-driven, 8q24 gain cancers.

This disclosure further identifies a PVT1_212 splice variant peptide encoded upon circularization (PEPc) and a peptide encoded by the linear form ($PEP_L$). In a further embodiment, several antibodies against the C terminal of PEPc and $PEP_L$ which can identify endogenous expression of the PEPs are provided. In some embodiment, these antibodies are used against the PVT variations for histopathology, research, and diagnostic purpose for 8q24 gained, MYC-driven cancers. Further provided are inhibitors against the PEPs (PEPc and $PEP_L$).

Provided herein is a method of detecting a novel PVT-1 splice variant in a biological sample. The method of detection involves: obtaining a biological sample from a subject, isolating a nucleic acid from the biological sample that comprises genomic DNA, and analysis for the presence or absence of the PVT-1 splice variant. In some embodiments, the method comprises detection of a protein product or a peptide encoded by the splice variant that distinguishes the splice variant from the wild type form. In some embodiments such detection involves using an antibody for western hybridization or in situ hybridization detection methods. In some embodiments, the novel PVT-1 splice variant is a circular PVT-1 transcript product. In some embodiments, the novel PVT-1 splice variant is a circular PVT-1 translated product. Identification of the novel PVT-1 splice variant indicates presence of a cMYC driven cancer in the subject.

In some embodiments, identification of any one of the PVT1 splice variants indicated in the above section of the disclosure described herein in a biological sample from a subject is indicative of a MYC-driven cancer in the subject. In some embodiments, identification of Circ PVT1 in a sample from the subject is indicative of a MYC-driven cancer in the subject. In some embodiments one or more PVT1 splice variants can be identified. In some embodiments one or more PVT1 splice variants can be the 104 amino acid PEPc in a biological sample of a subject is indicative of a MYC driven cancer in the subject.

In some embodiments identification of any one or more of the PVT1 splice variant identified in the disclosure is complemented with an additional mode of analysis of a biological sample from the subject for determination of c-MYC driven cancer in a subject.

In some embodiments identification of any one or more of the PVT1 splice variant identified in the disclosure is complemented with one or more physiological evaluations of the subject for determination of c-MYC driven cancer in a subject.

In some embodiments identification of any one or more of the PVT1 splice variant identified in the disclosure is complemented with one or more biochemical evaluations of the subject for determination of c-MYC driven cancer in a subject.

In some embodiments, identification of any one or more of the PVT1 splice variant is performed by analysis of RNA. In some embodiments, qRT-PCR analysis is used for the identification. In some embodiments the identification of any one or more of the PVT1 splice variant is performed by analysis using a PVT1-splice variant specific antibody for determination of c-MYC driven cancer in a subject.

In some embodiments provided herein is a method for treating a subject having a MYC-driven cancer, the method comprising: (a) determining the presence of one or more PVT1 splice variant in a biological sample from the subject, wherein the PVT1-splice variant augments c-MYC expression; (b) administering to the subject a therapeutic composition for the MYC-driven cancer.

Also provided herein is a kit for determining a PVT1 splice variant in a biological sample of a subject.

EXAMPLES

The examples below further illustrate the described embodiments without limiting the scope of the disclosure.

Figure 2:
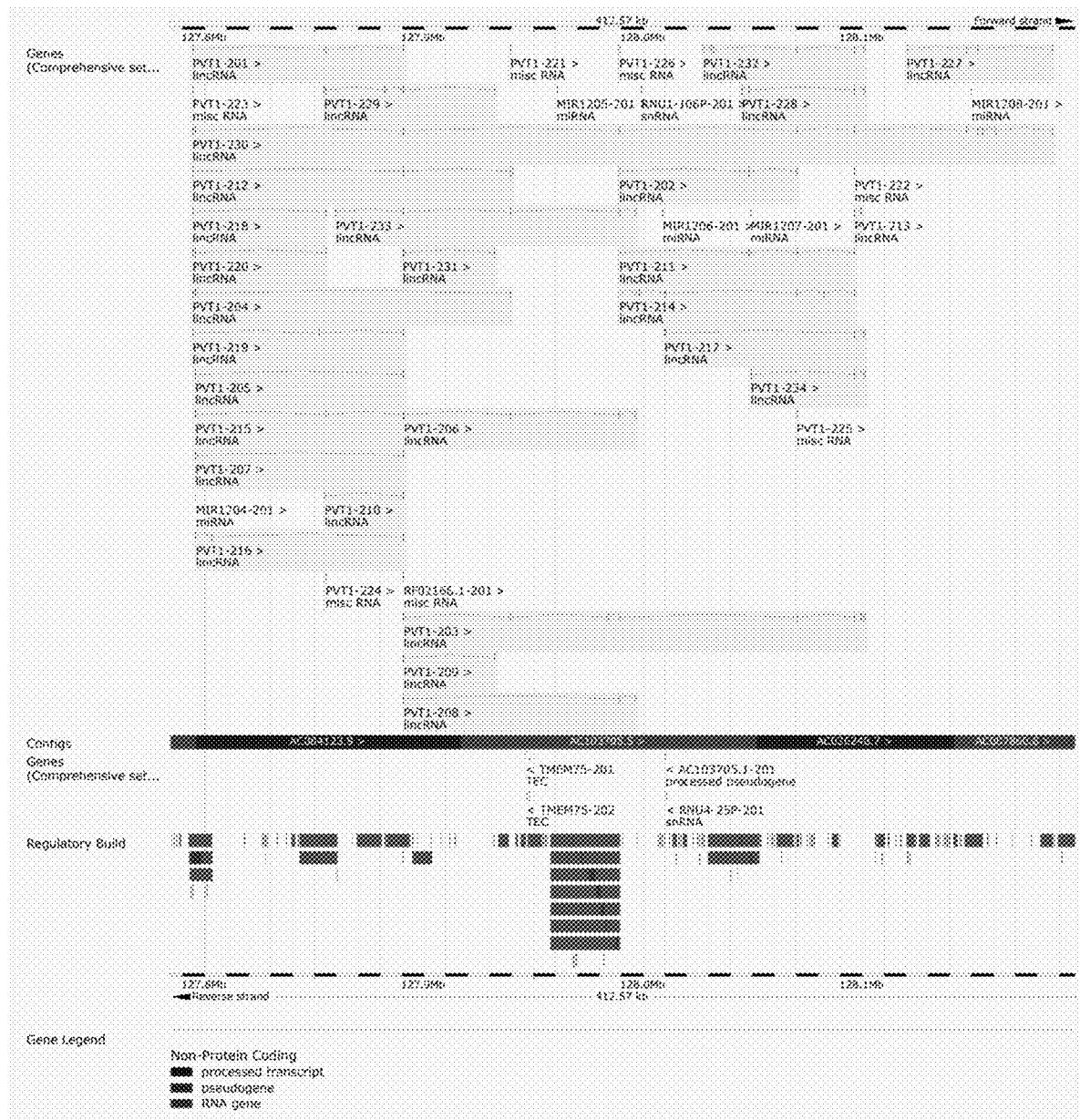
FIG. 2 is a pictograph of chromosomal maps shows PVT1 splice variants.
Figure 3:
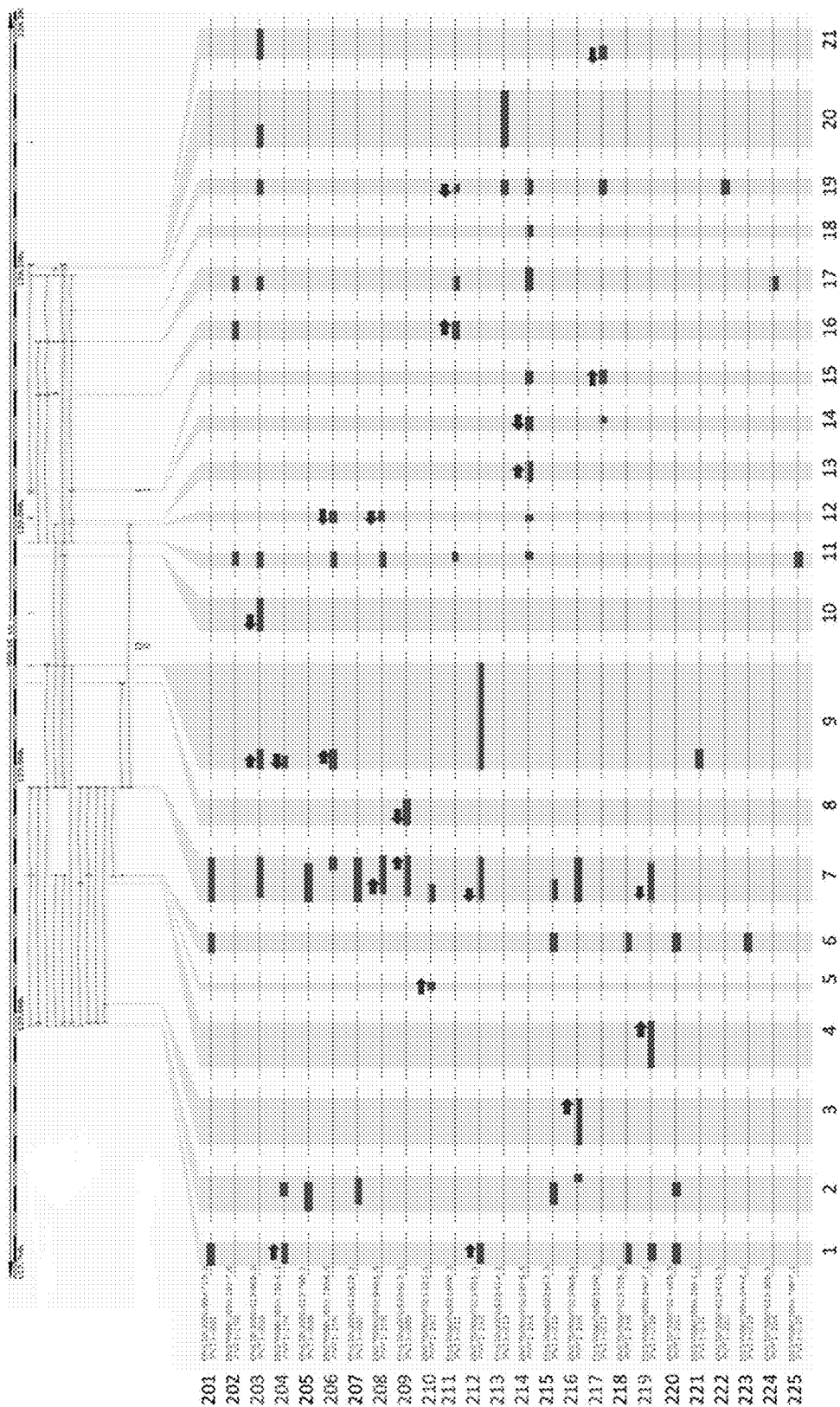
FIG. 3 shows a PVT1 splice variant screen.
Figure 7:
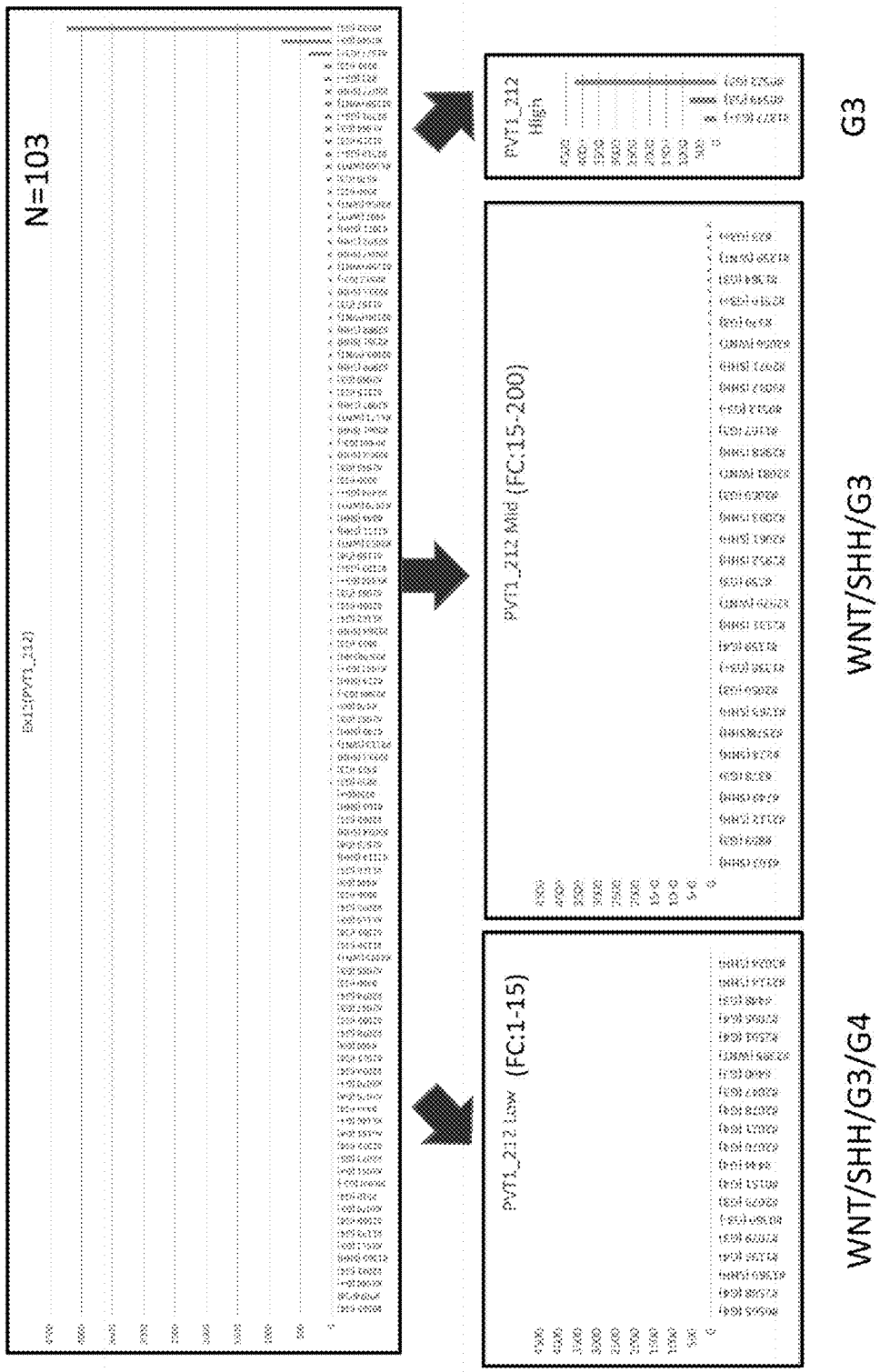
FIG. 7 shows representative data of exemplary expression of PVT1_212 in MB-PDX samples.
Figure 11:
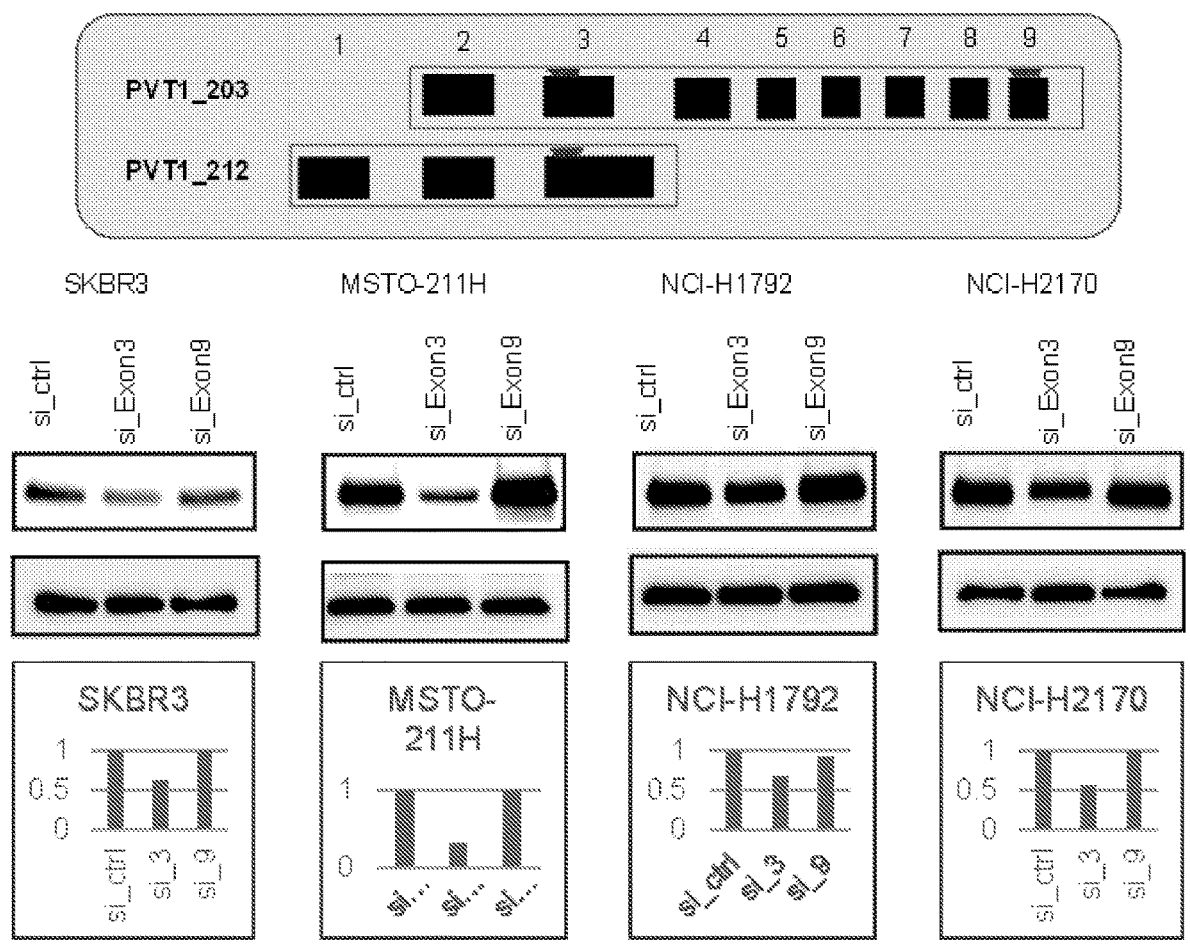
FIG. 11 shows representative data indicating the effect of siRNAs against PVT1 exons in 8q24 cell lines.

Example 1: Identification of the PVT1 Splice Variant Responsible for Stabilizing MYC Protein in Human Cancers The ENSEMBLE database was searched in order to identify the variants that regulate MYC protein in cancer cells. Accordingly, 25 splice variants of PVT1 have been found (FIG. 2). Primers were developed to identify the abundance of each transcript in patient derived medulloblastoma (MB) xenografts (PDX) (FIGS. 3 and 4). The analysis suggested that PVT1_212 is the most abundant PVT1 splice variant in all the 4 subgroups of the MB PDXs, while PVT1_203 being the second most prevalent splice variant. PVT1_212 is most prevalent in the MB Subgroup 3 patients, which has the poorest prognosis among the MB patients (FIG. 5). Three types of PVT1_212 expression pattern were identified in MB PDXs as well in patient samples: Low PVT1_212 expressing group (0-15×): contained mainly Subgroup 4 MBs, Intermediate PVT1_212 expressing group (15-200×): contained Subgroups 3, Shh and Wnt MB, and the high PVT1_212 expressing group (200-1000×): Exclusively Subgroup 3 (FIGS. 6 and 7). This demonstrated that PVT1 expression can be used to stratify MB patients, where the high PVT1_212 expressing group (200-1000×) can designate the 8q24 gain, MYC-driven type of the Group 3 MB patients (generally associated with the poor prognosis).

Example 2: Functional Identification of the PVT1 Exons Regulating MYC Protein in Human Cancers For this study, si-RNAs against exon 2, 3 and 9 of the annotated PVT1 gene were designed. Among these, exon 9 exclusively belongs to PVT1_203, whereas exon 2 and 3 is shared between PVT1_212 and PVT1_203. Knock down of PVT1 using si-RNAs against exons 2 and 3, but not Exon 9, reduced MYC protein by as much as 75% (MSTO) to 40% (NCI-H1792) (FIGS. 8, 9, 10, and 11). This demonstrated that PVT1_212, and not PVT1_203 was responsible for MYC augmentation in 8q24 gain cancers, and targeting the product of PVT1_212 can significantly reduce the MYC protein levels in these cancers.

Figure 12A:
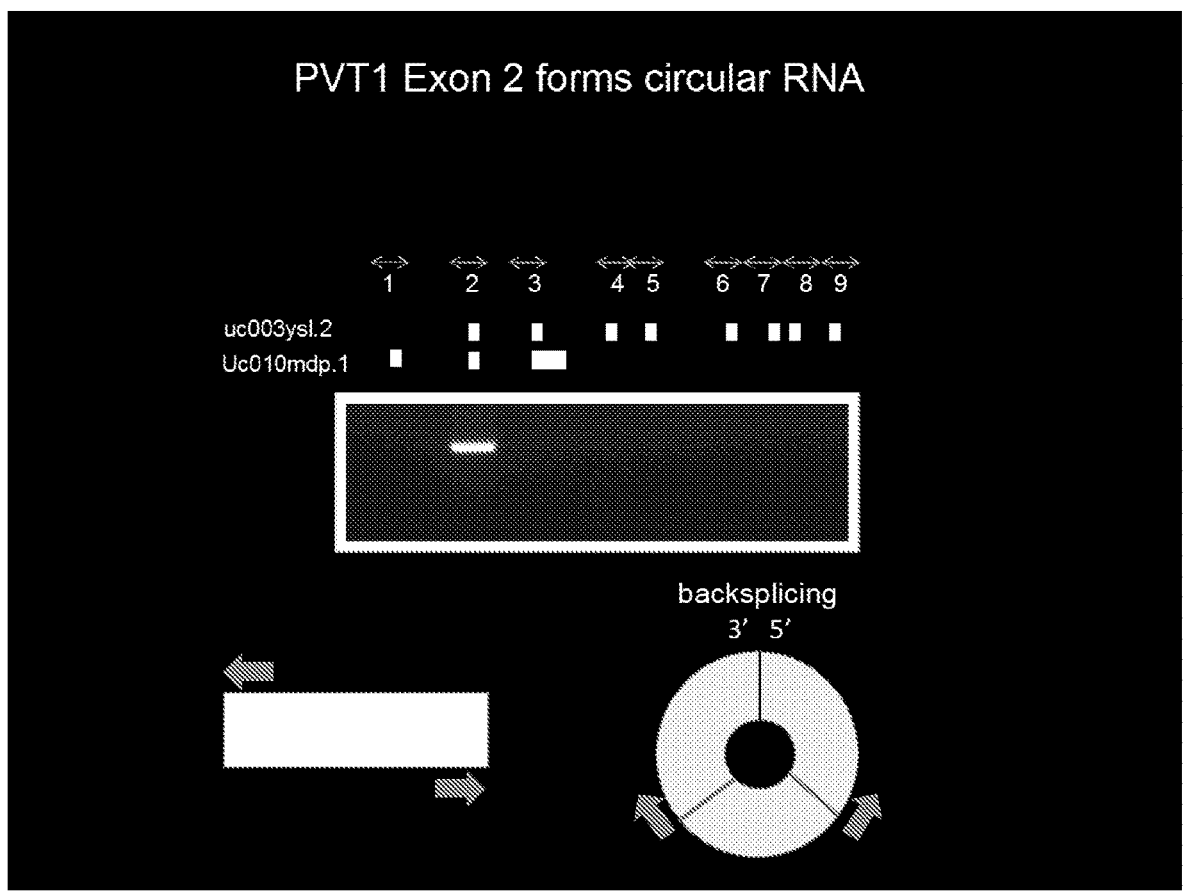
FIG. 12A shows a graphic representation indicating that PVT1 exon 2 forms circular RNA.
Figure 12B:
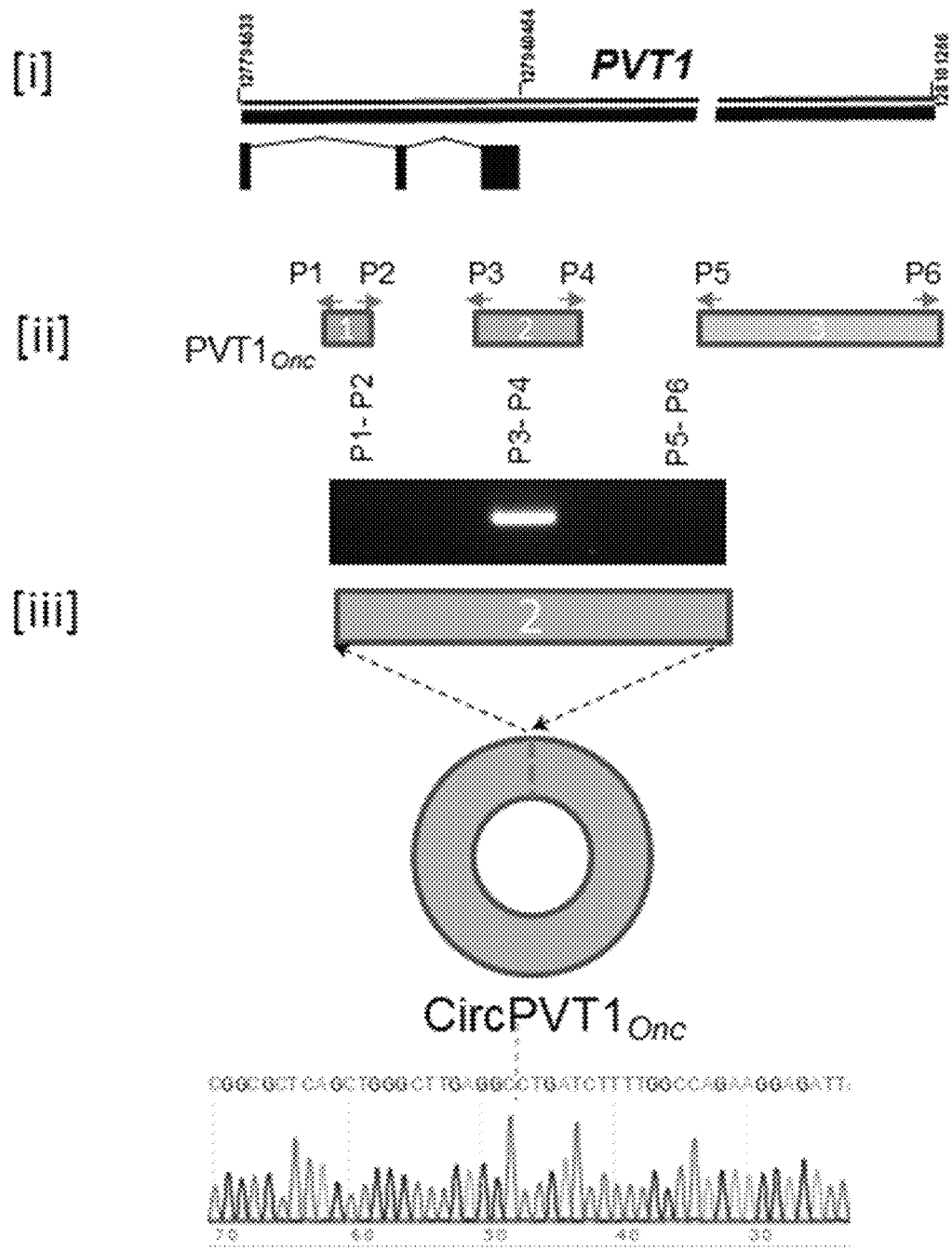
FIG. 12B is a graphical representation indicating that PVT1_212 consists of three exons and span over Ch8: 127794533-Ch8:127940454 (FIG. 12 B[i]). Divergent primers are designed for each exon (FIG. 12B[ii]). cDNA was derived from total RNA using random hexamers and sequenced (FIG. 12B[iii]).
Figure 13:
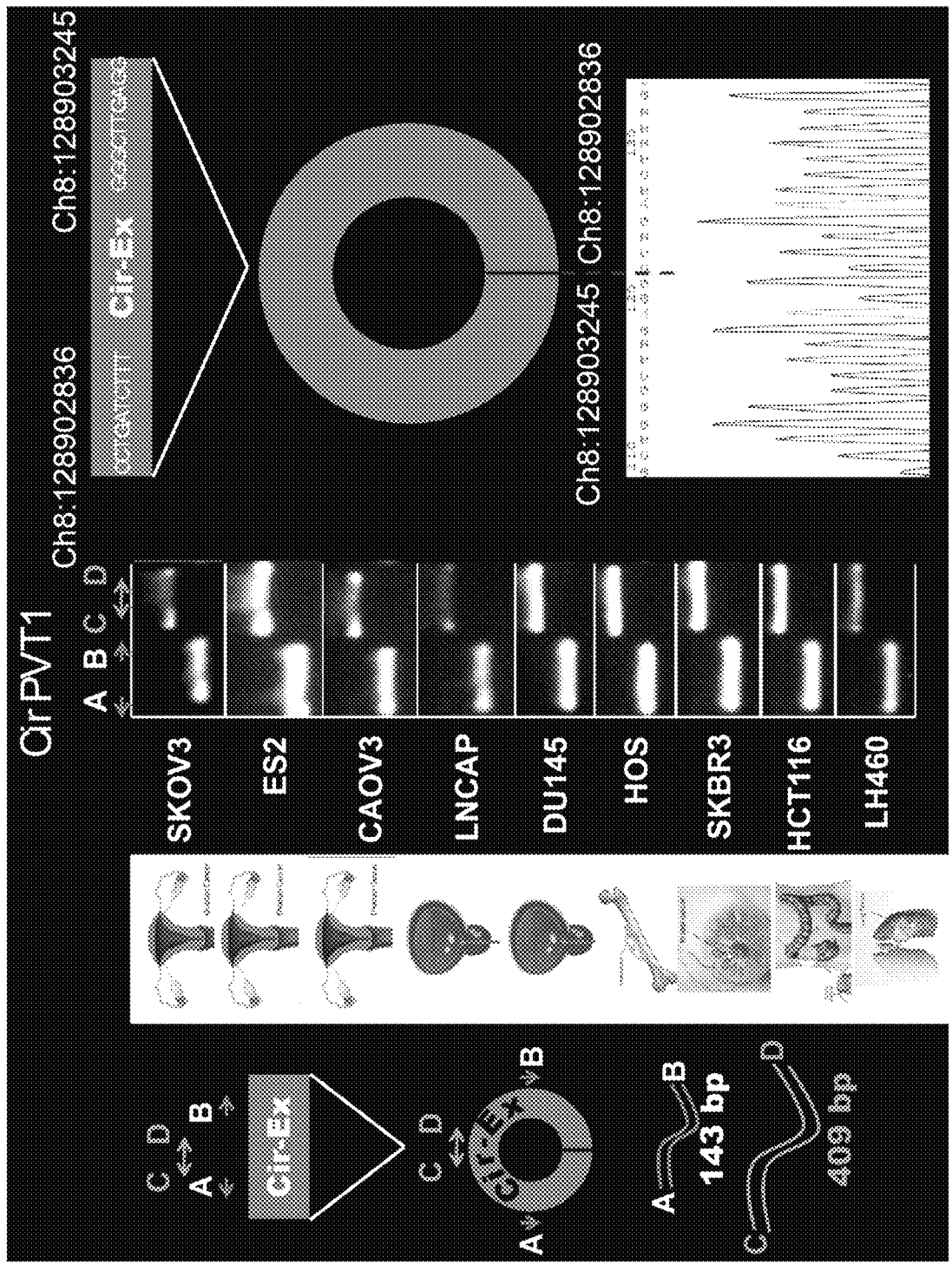
FIG. 13 shows the circular PVT1 RNA (SEQ ID NO: 1) in various cell lines.
Figure 14:
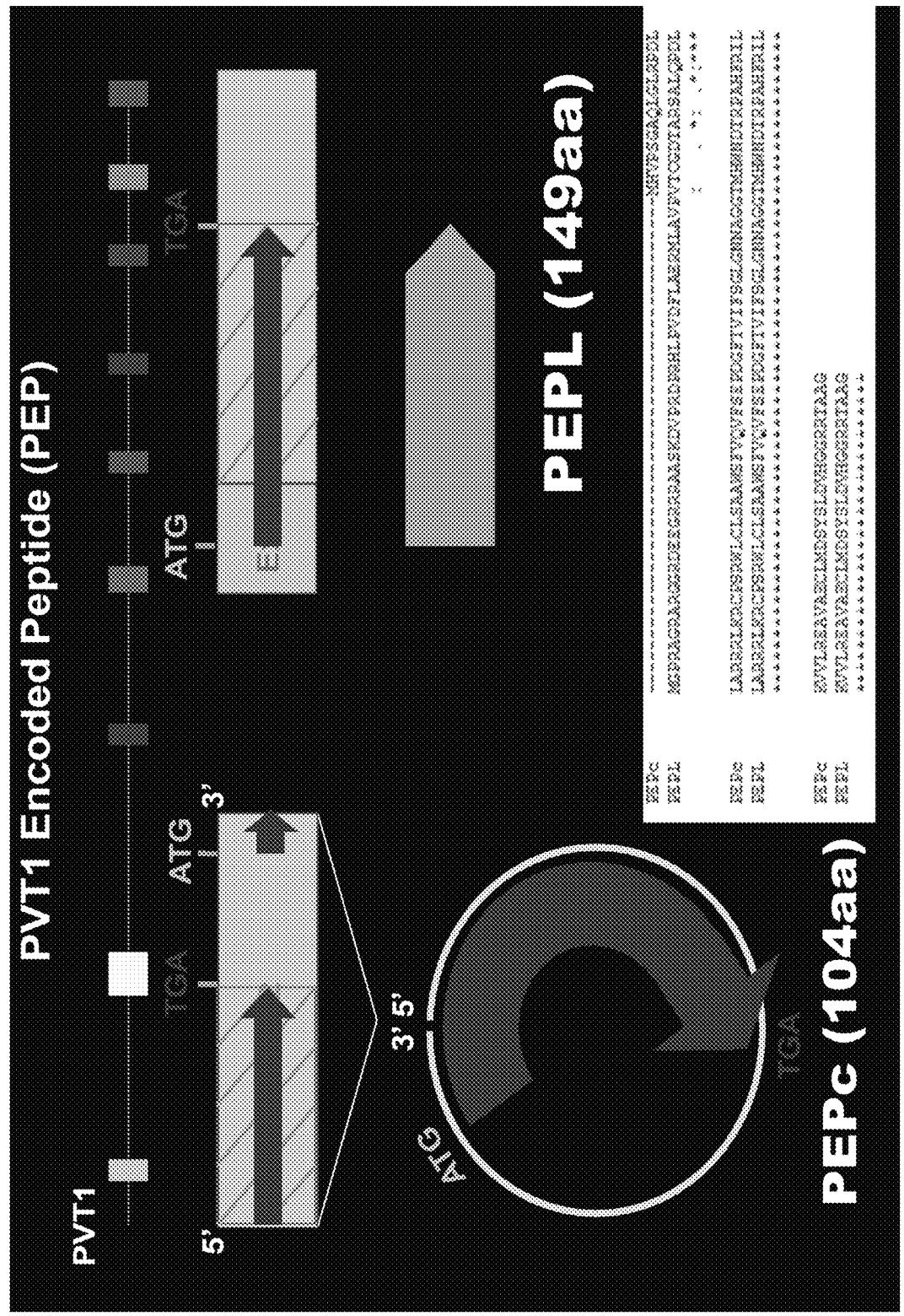
FIG. 14 is a graphical representation that shows the structure of PEP. PEPc (SEQ ID NO: 33) and $PEP_L$ (SEQ ID NO: 34) are shown.
Figure 15:
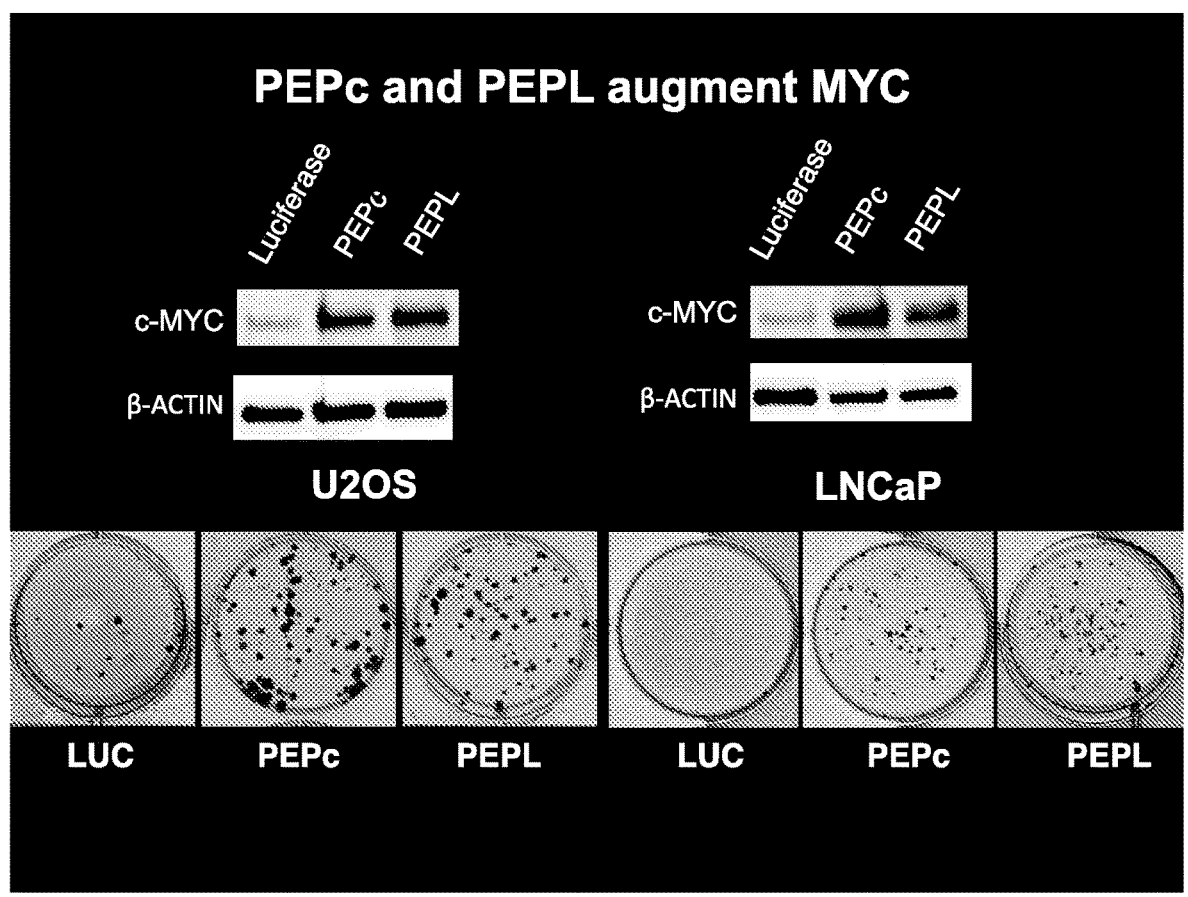
FIG. 15 shows data indicating PEPc and $PEP_L$ augment MYC levels in U2OS and LNCaP cells. Upper panel, Western blot analysis; Lower panel represents colony formation of PEPc or $PEP_L$ or control vector Luc expressing U2OS and LNCaP cells in soft agar cultures.
Figure 16:
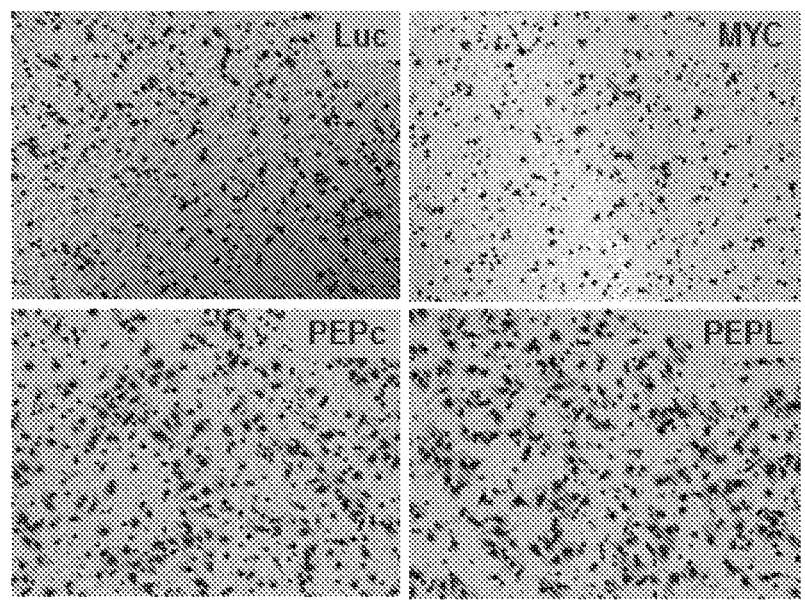
FIG. 16 shows representative data indicating the results of transwell migration experiment in U2OS cells.

Example 3: PVT1_212 Codes for Novel Peptides that Augment MYC in 8q24 Gain Cancers This study demonstrated exon 2 of the PVT1 gene can undergo back-splicing and form a circular RNA (CircPVT1_212) (FIGS. 12A-C and 13). As shown in FIG. 12A and FIG. 12B(i) PVT1_212 consists of three exons and span over Ch8:127794533-Ch8:127940454. FIG. 12B(ii). cDNA was derived from total RNA obtained from cancer cells using random hexamers (it is important to use random hexamers, since circular RNAs do not have poladenylated 3' sequence). Divergent primers were designed for each exons of PVT1_212 to identify the CircPVT1 arising from exon 2 of PVT1_212. Sequencing of the CircPVT1 junction confirmed that the junction sequence emanated from the 3' and 5' ends of PVT1_212 (FIG. 12B(iii) and FIG. 12C). Cloning the splice junction demonstrated that this circle emanates from PVT1_212 and not PVT1_203, since the latter starts from ~150 bp downstream of the beginning of the Exon 2 (FIG. 13). It was found that upon circularization, CircPVT1_212 can form a protein coding ORF of 104 amino acids. The potential peptide was designed as PVT1 Encoded Peptide upon Circularization (PEPc). It was also found that PVT1_212 can encode another peptide (from Exon 1 and 2) of 149 amino acids, which share the same ORF with PEPc for the 94 amino acids at their C terminal end. This variant was designed as PVT1 Encoded Peptide linear form ($PEP_L$) (FIG. 14). Exogenous addition of PEPc and/or $PEP_L$ was seen to augment MYC in U2OS and LNCaP cells, and increase their transformation and metastatic potential (FIGS. 15 and 16).

Figure 17:
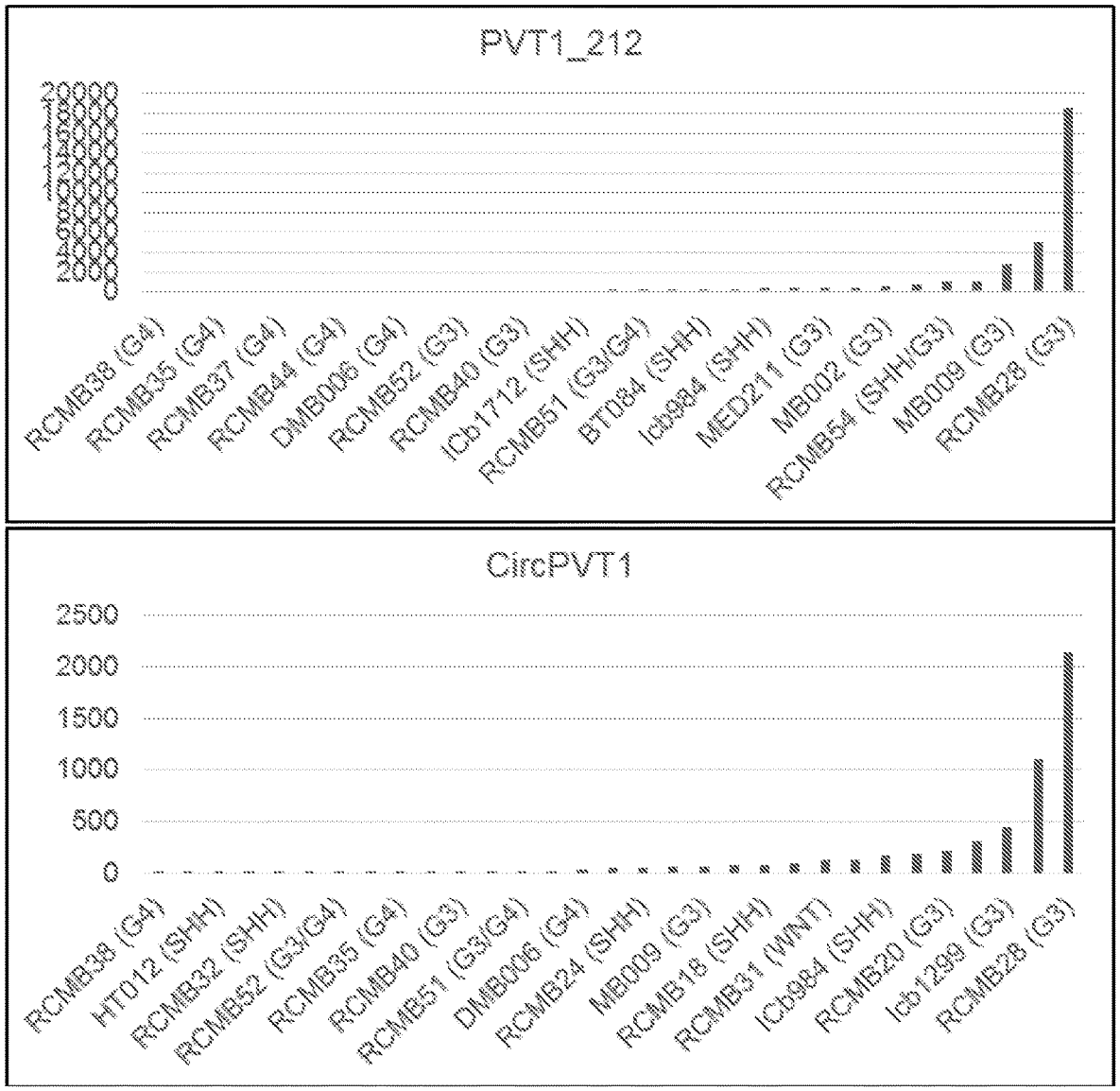
FIG. 17 shows representative data indicating similar expression of PVT1_212 and circularPVT1 in MB PDX samples.
Figure 18:
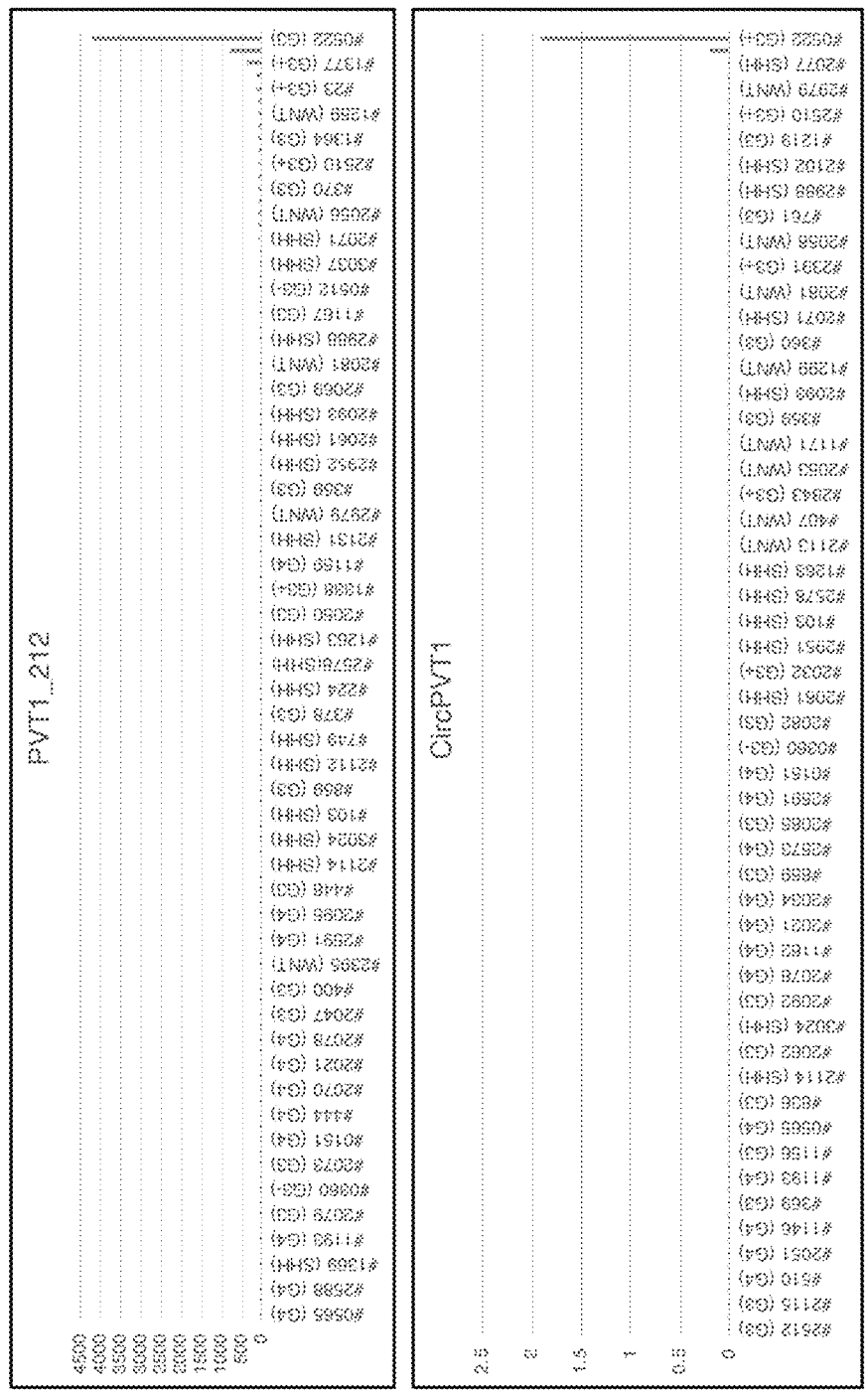
FIG. 18 shows representative data indicating similar expression of PVT1_212 and circularPVT1 in MB tumor RNA.
Figure 19:
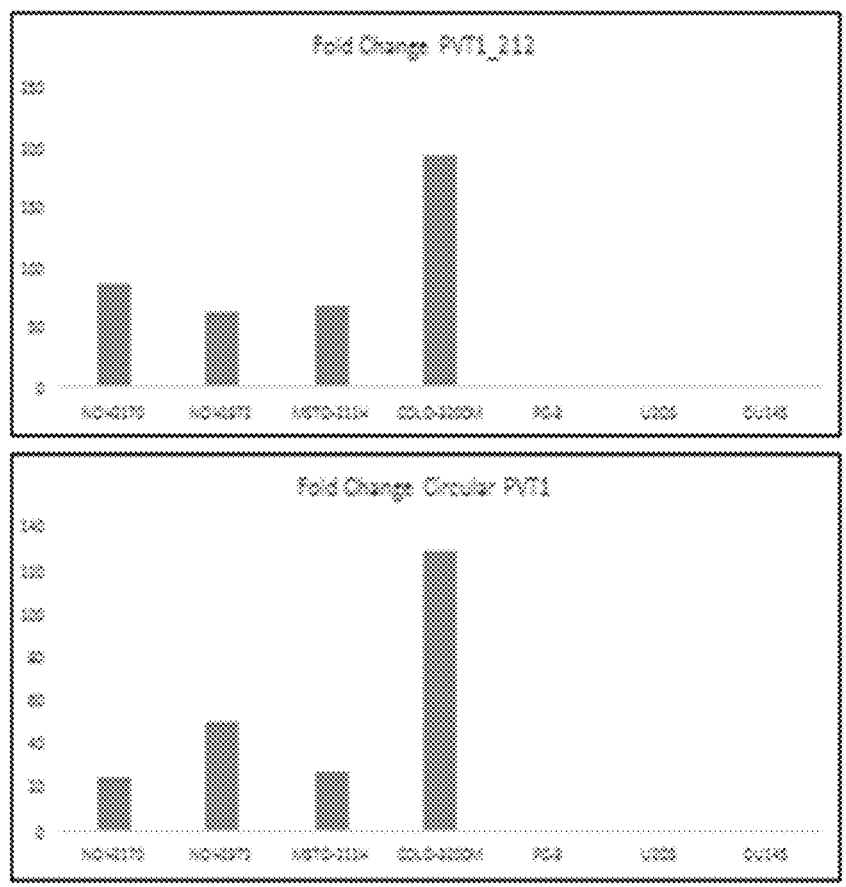
FIG. 19 shows representative data indicating expression of PVT1_212 and circular PVT1 in high and low copy number 8q24 cell lines.
Figure 20:
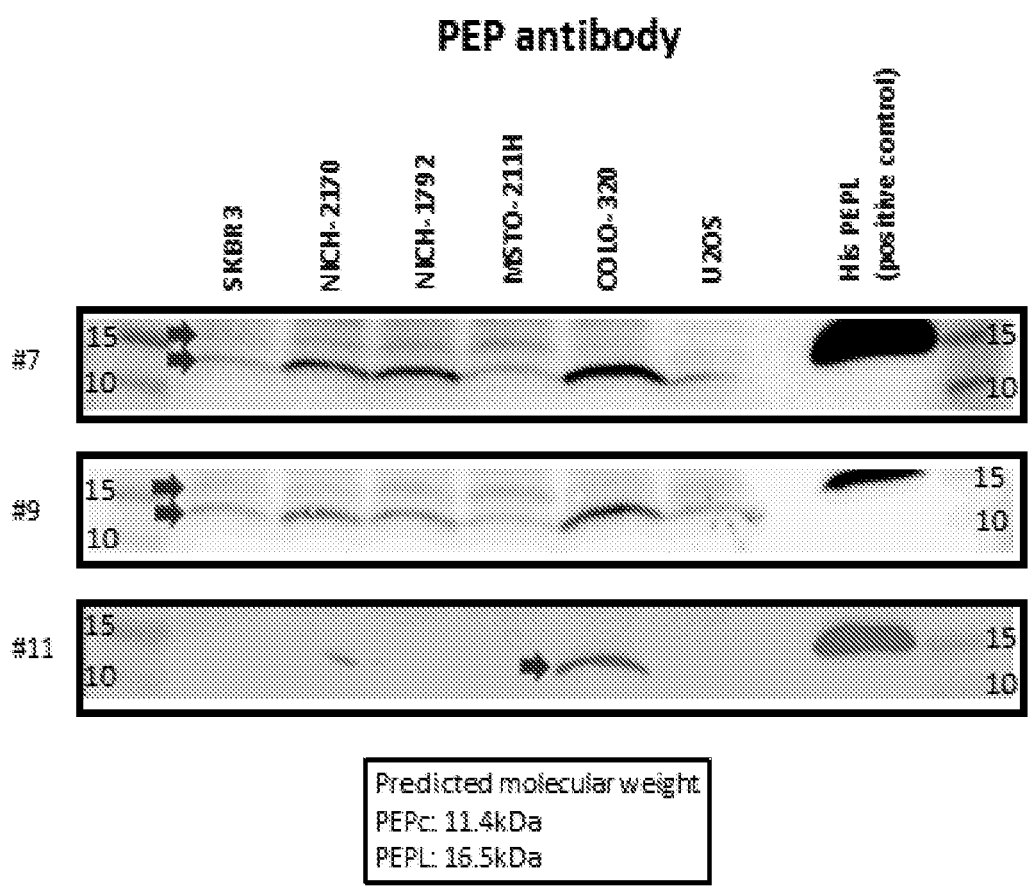
FIG. 20 shows specificity of PEP antibody.
Figure 21:
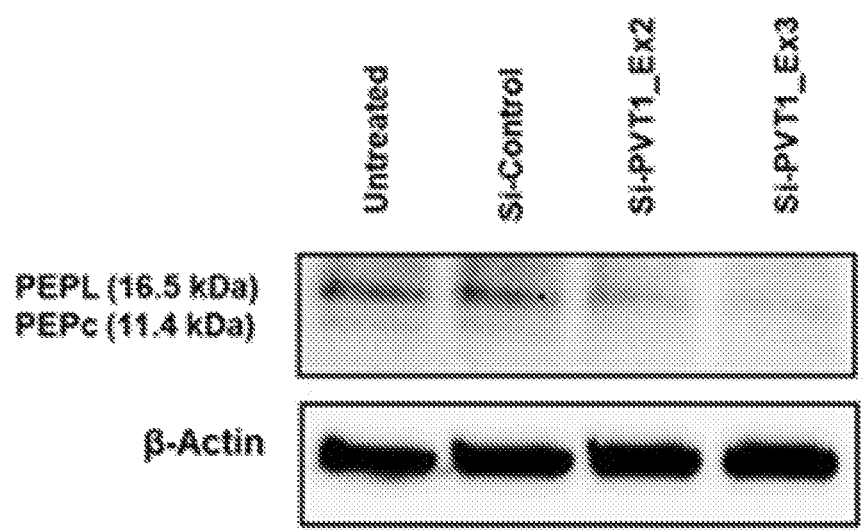
FIG. 21 shows a western blot identifying PEP.
Figure 22:
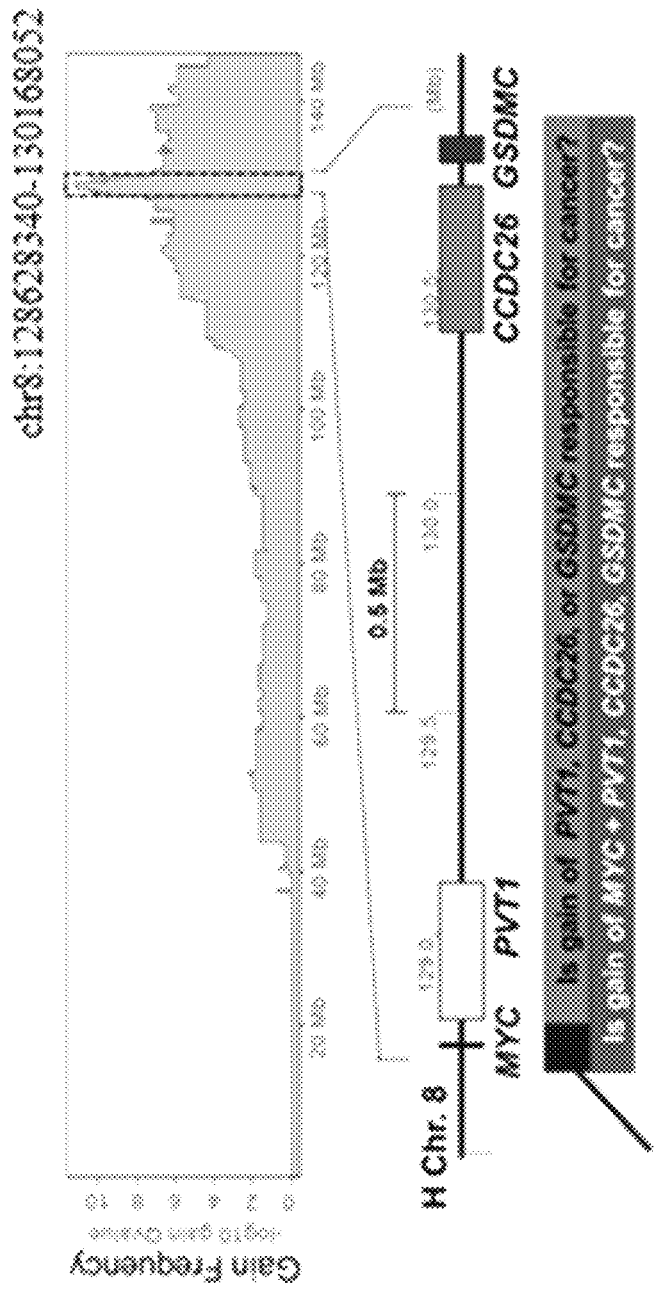
FIG. 22 shows gain of 8q24 is a common amplified region in human cancer.
Figure 23:
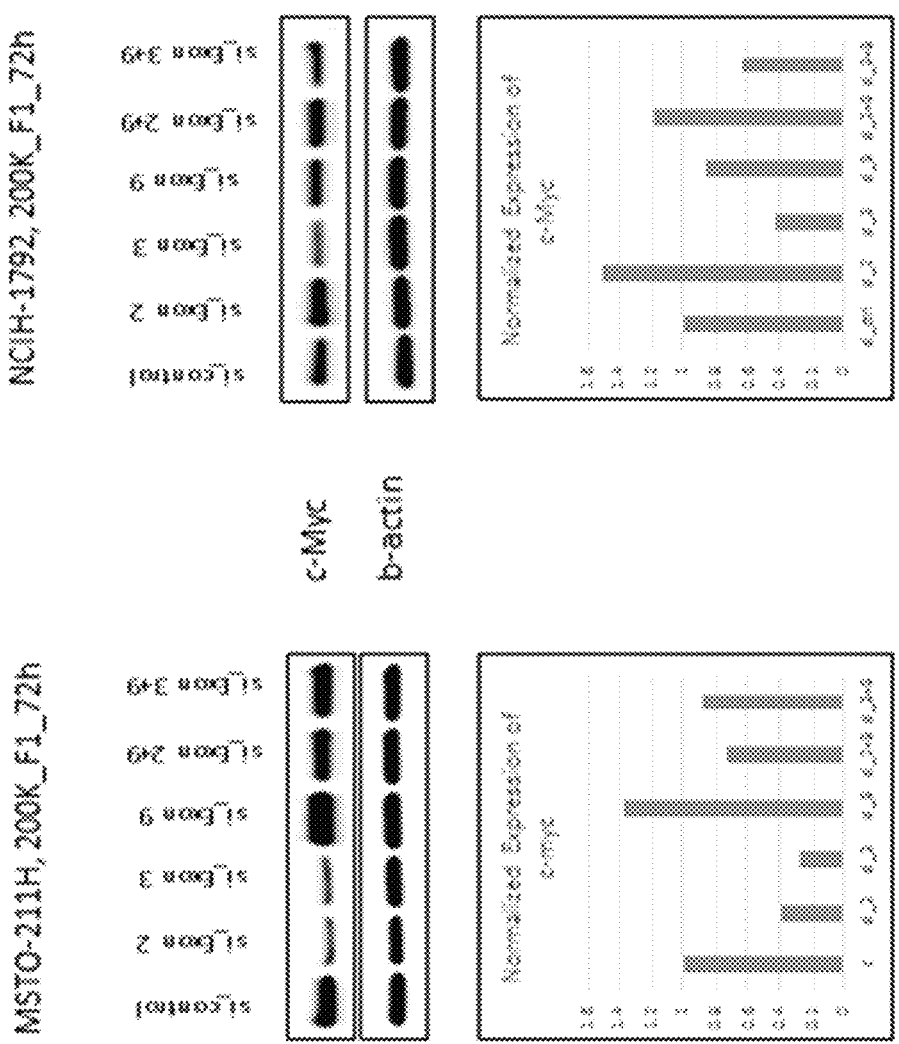
FIG. 23 shows representative data indicating effect of siRNAs against PVT1 exons in MSTO and NCIH1792 cells.
Figure 24:
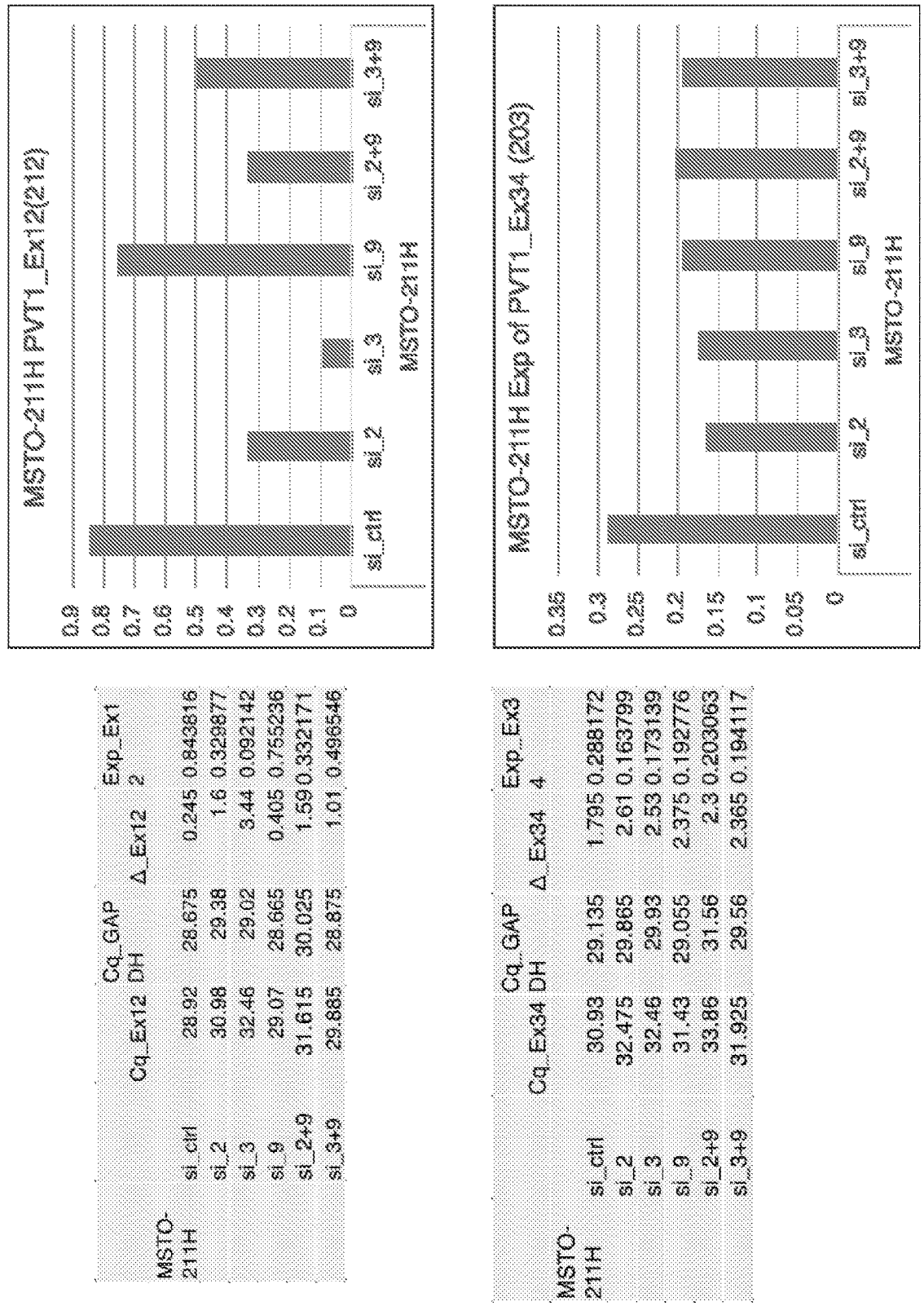
FIG. 24 shows representative data indicating effect of siRNAs against PVT1 exons in MSTO and NCIH1792 cells.
Figure 25:
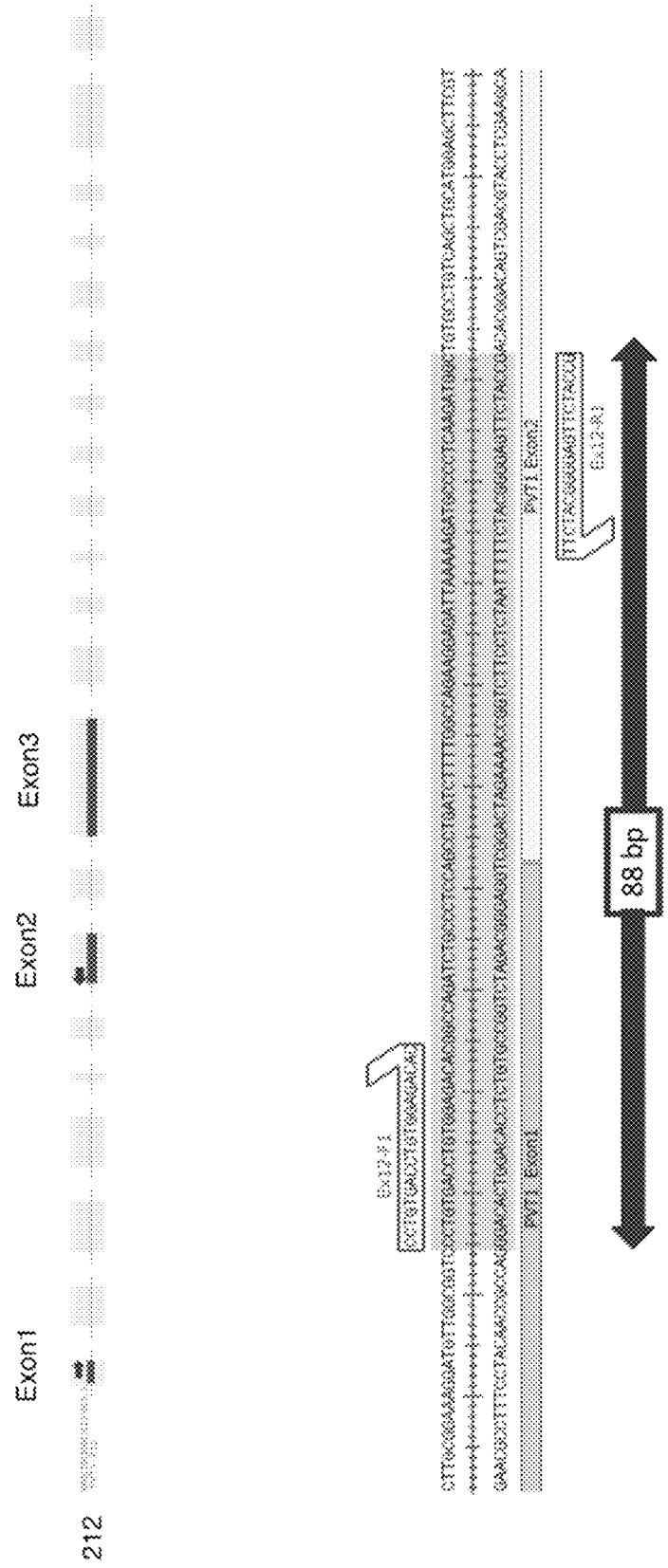
FIG. 25 shows splice junction between exons 1 and 2 of PVT1. A portion of PVT1_212 is shown below (SEQ ID NO: 36). The amplicon (88 bp; SEQ ID NO: 45) is spanning PVT1 exon 1-2 junction, which contains Ex12-F1 (SEQ ID NO: 35) in exon 1 and Ex12-R1 (SEQ ID NO; 37) in exon 2.
Figure 26:
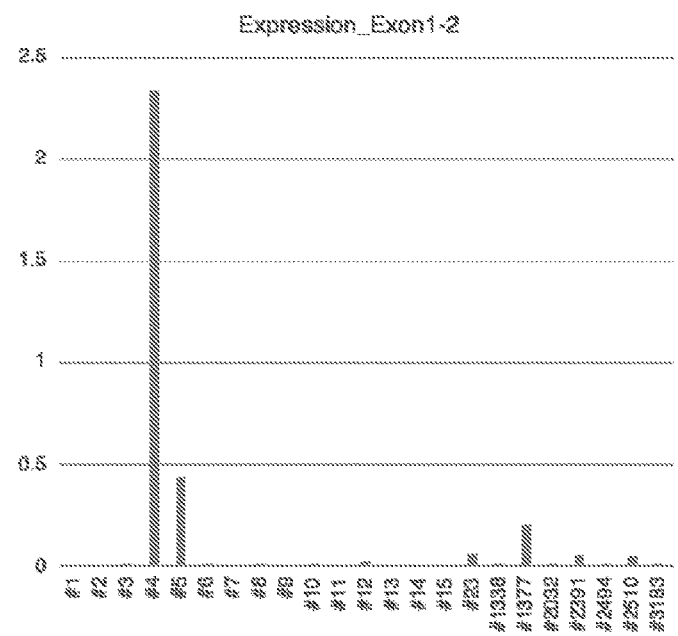
FIG. 26 shows results for RT-qPCR on MB samples.
Figure 27:
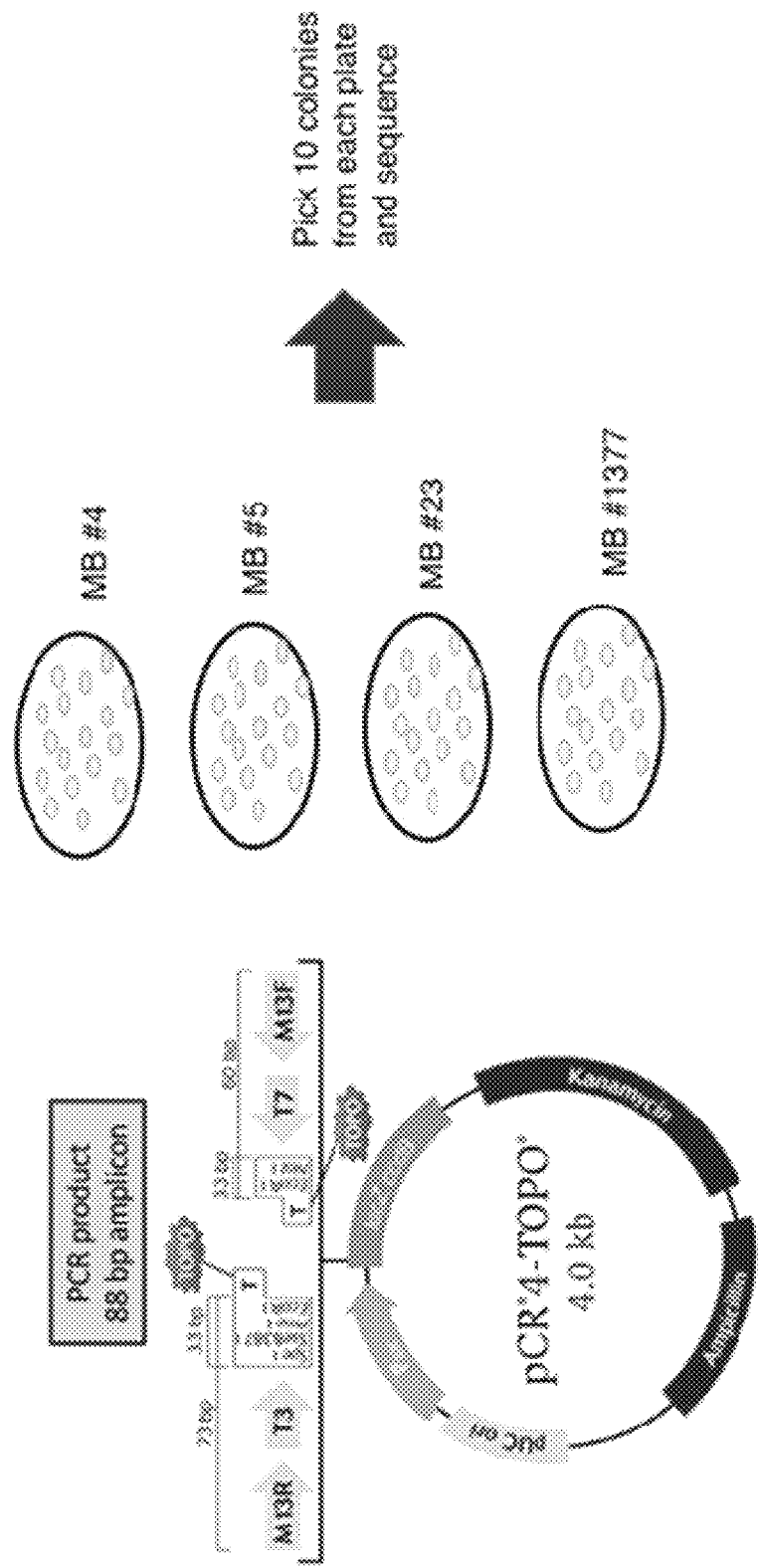
FIG. 27 shows cloning of amplified sequences.

The expression pattern of CircPVT1_212 was investigated in MB PDXs as well as patient samples, and it was observed that the expression of CircPVT1_212 correlates identically with PVT1_212 expression (FIGS. 17, 18, and 19). Since circular RNAs are typically more stable than linear RNAs due to their resistance to exonucleases, and can be identified in blood/plasma derived patient samples, this demonstrated that CircPVT1_212 can be used as a liquid biopsy marker for MYC-driven, 8q24 gain cancers. Finally, several antibodies against the C terminal of PEPc and $PEP_L$ were derived which can identify endogenous expression of the PEPs (FIGS. 20 and 21). Specificity of these antibodies was confirmed by knocking down PVT1_212 (FIG. 21). This demonstrated that the antibodies against PEPs can be used for histopathology, research and diagnostic purpose for 8q24 gained, MYC-driven cancer. FIG. 22 shows gain of 8q24 is a common amplified region in human cancer. In an exemplary assay, siRNAs that can bind to Exons 2, 3, 9, 20 and 30 of PVT1 were separately expressed in cancer cell lines MSTO and NCIH1792. It was observed that only siRNA directed to the Exon 2 and Exon 2 showed remarkable reduction in MYC protein levels (FIG. 23). FIG. 24 shows effect of siRNAs against PVT1 exons on mRNA expression of Myc in MSTO and NCIH1792 cells. FIG. 25 shows splice junction between exons 1 and 2 of PVT1. Expression of Exons 1 and 2 were determined by RT-qPCR on Medulloblastoma (MedullB) samples, as shown in FIG. 26. The splice variants are PCR amplified with suitable primers and cloned in Topo vectors for sequence analysis as shown in FIGS. 27-29. FIG. 29 shows sequence analysis of highest expression variants.

FIG. 29 shows sequence analysis of highest expression variant.

Example 4: Circ PVT1 in MYC Cancers

Figures 30A, 30B:
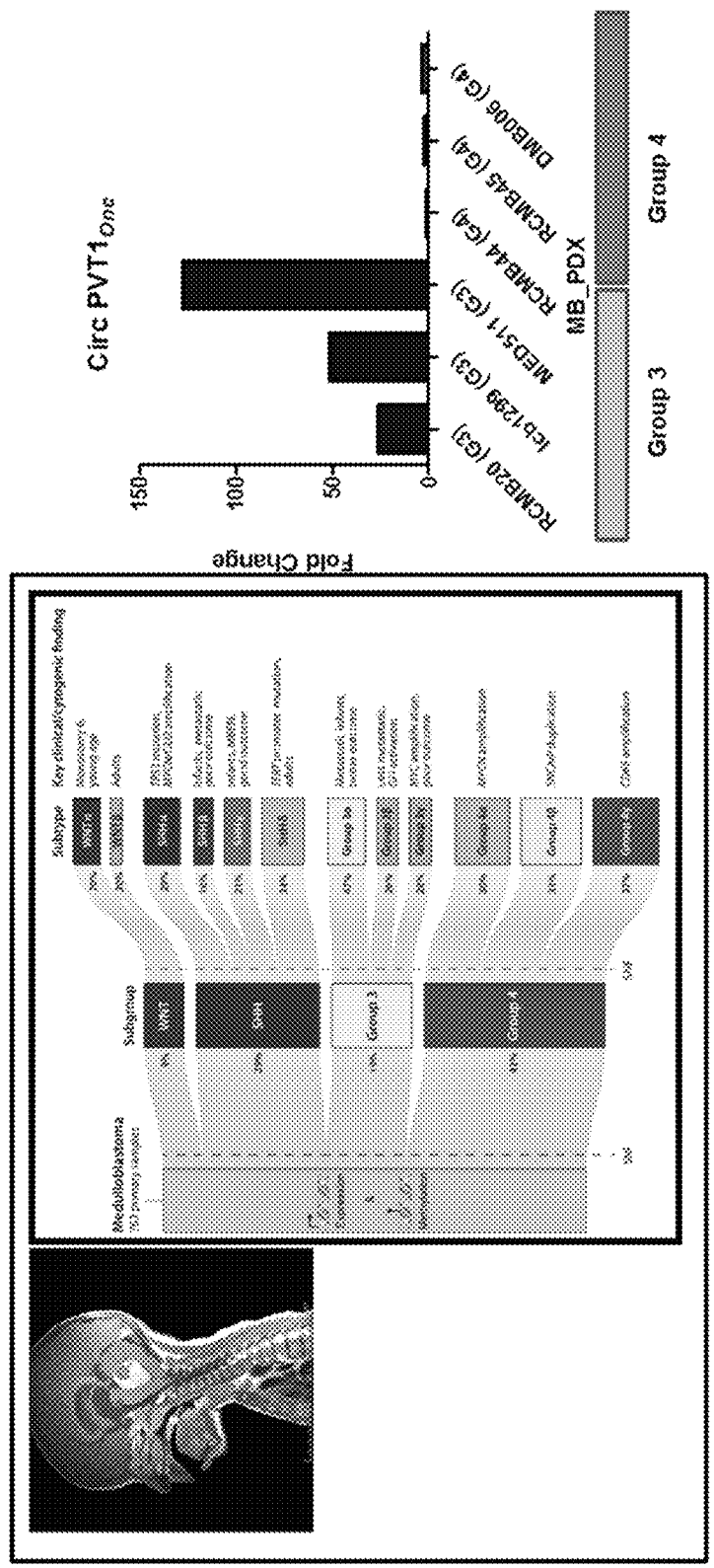
FIG. 30A represents an existing standard for grouping and classification of medulloblastoma tumors.
FIG. 30B shows representative quantitative RT-PCR of expression of CircPVT1 in Group 3 and Group 4 medulloblastoma tumors.

Expression of the CircPVT1 was further investigated in patient tissue samples. CircPVT1 is enriched in MYC driven Group 3 medulloblastoma tumors. FIG. 30A subgroup of Group 3 medulloblastoma harbor MYC amplification and have the worst clinical outcome compared to the other medulloblastoma groups (Cavalli et al, Cancer Cell, 31:737-754). FIG. 30B shows results from quantitative RT-PCR analysis of patient derived xenografts (PDX samples) from medulloblastoma patients (obtained from Dr. Weschler-Reya's lab at SBP). The results revealed that the CircPVT1 is especially enriched in the MYC driven Group 3 medulloblastoma tumors.

Figures 31A, 31B, 31C:
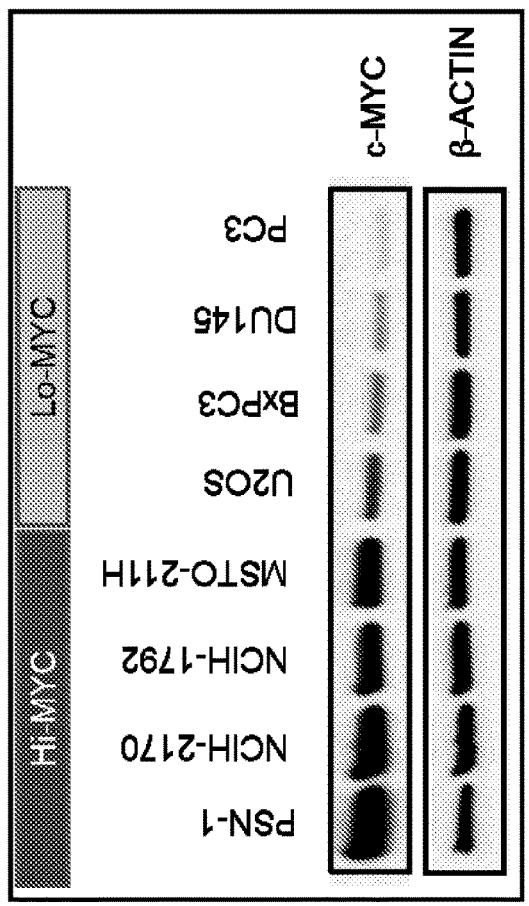
FIG. 31A represents data indicating correlation of copy number abundance of MYC and PVT1 in the indicated cancer cell lines.
FIG. 31B shows a western blot data for c-MYC expression and FIG. 31C shows representative quantitative RT-PCR data for expression of CircPVT1 in the cell lines.

High abundance of CircPVT1 is correlated to high MYC protein in multiple cancer cell lines. In order to examine whether abundance of CircPVT1 and MYC are correlated in multiple cancer cell lines, 4 cell lines were selected with high copy number of MYC and PVT1 (Hi-MYC cell lines: PSN-1, NCIH-2170, NCIH-1792, MSTO-211H) and 4 cell lines with MYC+PVT1 copy number neutral cell lines (Lo-MYC cell lines: U2OS, BxPC-3, DU145 and PC-3) from ATCC. These 8 cell lines represent a broad array of different types of cancers, as outlined in FIG. 31A. It was confirmed that the Hi-MYC cell lines are enriched in MYC protein, compared to the MYC protein in Lo-MYC cell lines (FIG. 31B). FIG. 31C shows results from q-RT-PCR which revealed that CircPVT1 is expressed in much higher levels in Hi-MYC cell lines compared to those in Lo-MYC cell lines.

Figure 32:
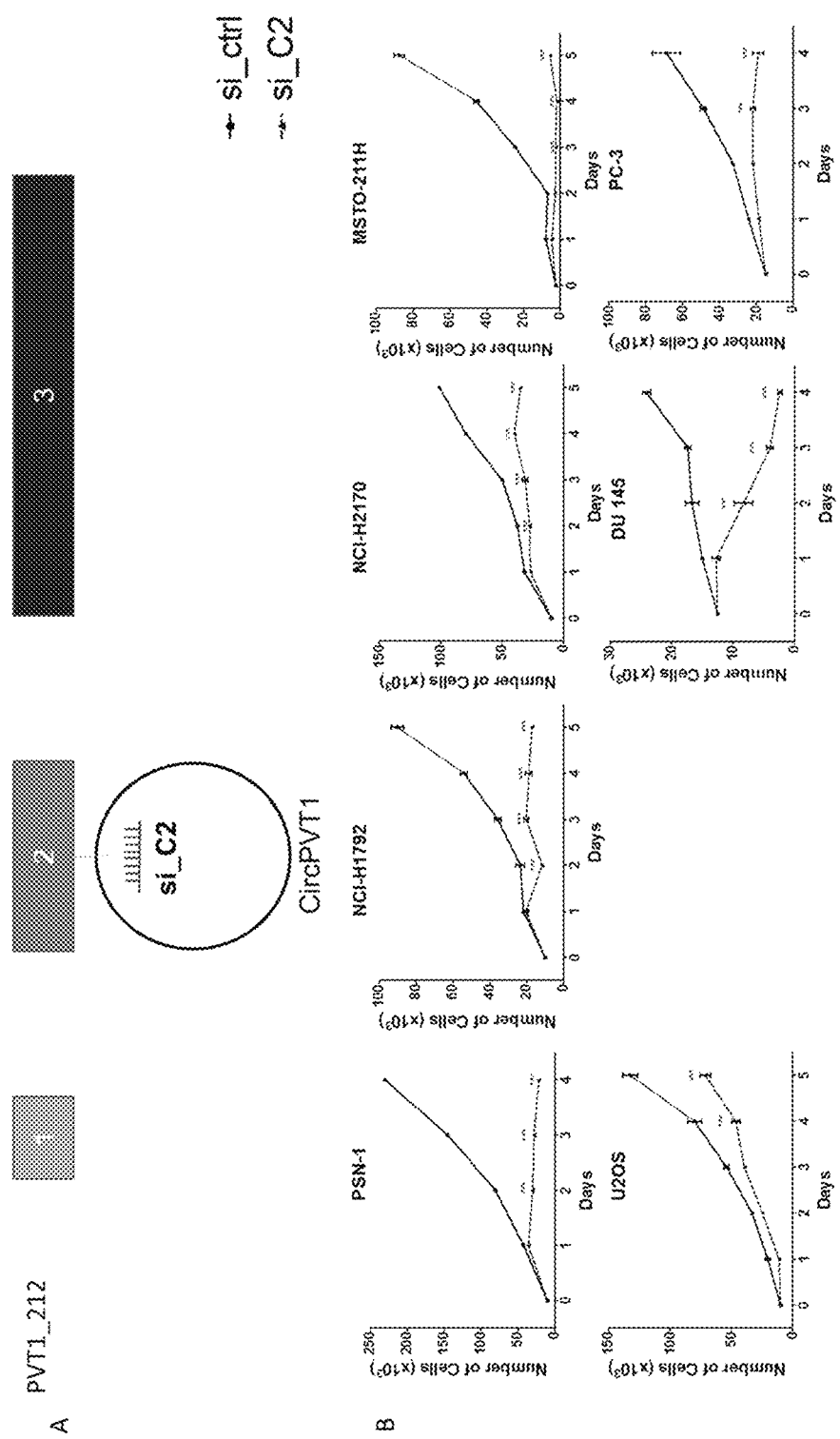
FIG. 32A shows a schematic diagram of siRNA design for control (siCtrl) or CircPVT1 inhibition (si_C2).
FIG. 32B shows data representing c-MYC expression in the indicated cell lines expressing either control (siCtrl) or CircPVT1 siRNA (si_C2).

Inhibition of CircPVT1 leads to growth arrest of Hi- and Lo-MYC cell lines. si-RNA was designed (si_C2) against the junction of the CircPVT1 which inhibits the expression of CircPVT1, but not that of PVT1_212 (FIG. 32A). Cell proliferation was assessed by counting cells following the transfection of the Hi-MYC and Lo-MYC cell lines with si_C2 (in red, also indicated by an arrow) and control si (si_Ctr, in blue) over the indicated period in the X-axis in in FIG. 32B. In each case, the siRNA directed to CircPVT1 (si_C2) inhibited proliferation of the MYC cell lines. The data demonstrates that the expression of the CircPVT1 is necessary for the proliferation of Hi-MYC as well as Lo-MYC cell lines, thus establishing the centrality of the CircPVT1 for the proliferation of cancer cells.

Figure 33:
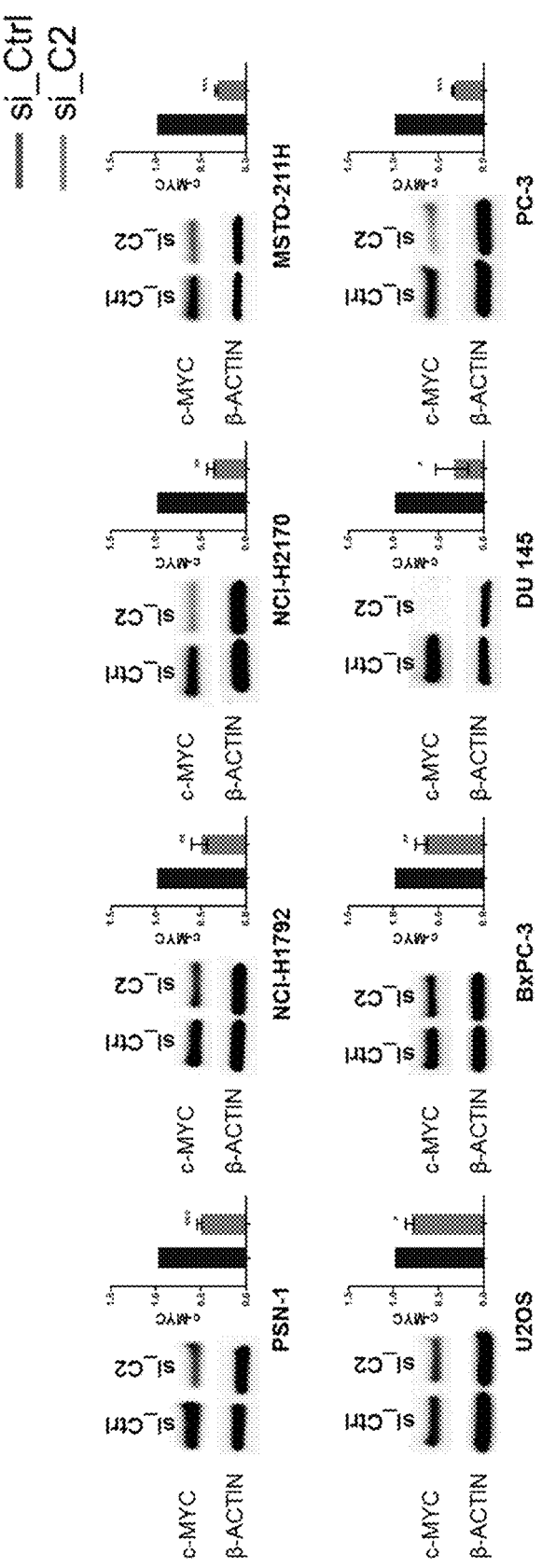
FIG. 33 indicates representative western blot data for MYC expression in each cell line as indicated expressing either control (siCtrl) or CircPVT1 siRNA (si_C2). Lower panel of each square block is a quantitative representation of the western blot expression data, where the solid black bars represent si Ctrl and the gray bars represents si_C2.

Next, it was investigated whether CircPVT1 can regulate MYC levels. Indeed, siRNA mediated knockdown of CircPVT1 in Hi- and Lo-MYC cell lines resulted in reduction in the MYC level in Hi-MYC as well as Lo-MYC cells, suggesting that CircPVT1 is required for MYC protein levels in cancer cells (FIG. 33).

Figure 34C:
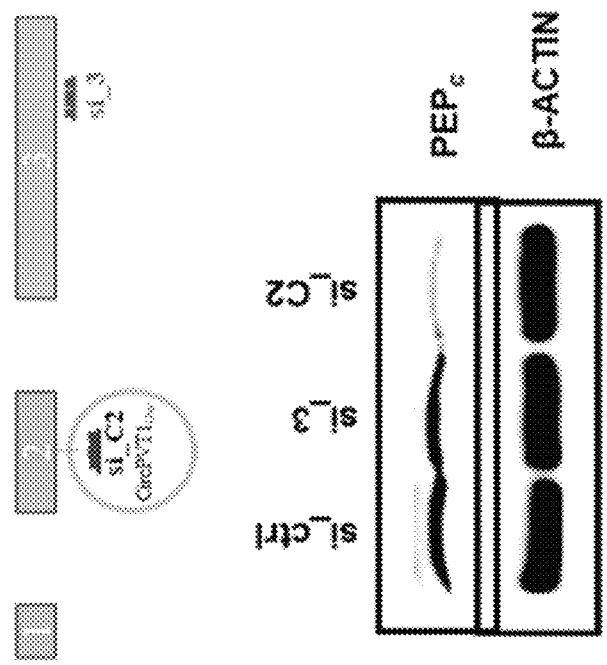
FIG. 34C shows data indicating effect of CircPVT1 siRNA (si_C2) on PEPc expression. 1, 2, and 3 represent the three exons of the splice variant PVT1_212. CircPVT1 arises from exon 2 of PVT1_212 and CircPVT1 codes for the peptide PEPc. si_RNA against CircPVT1, represented by si_C2, reduces PEPc protein but si_3, which knocks down the linear PVT1_212 does not reduce PEPc levels as shown in the Western Blot.
Figure 34B:
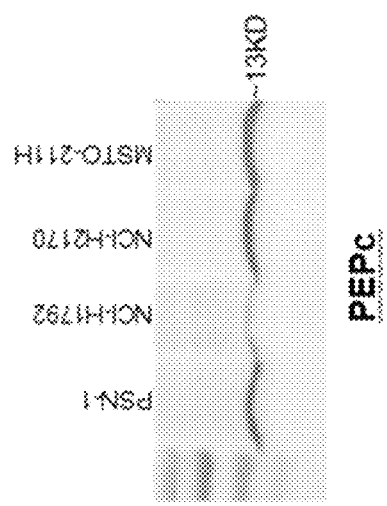
FIG. 34B shows western blot of PEPc/CJN protein.
Figure 34A:
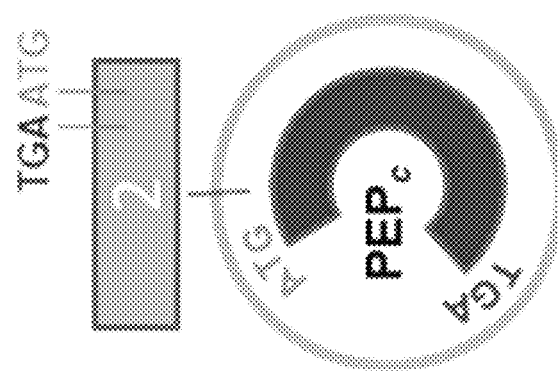
FIG. 34A is a graphical representation of the finding of an open reading frame in CircPVT1.

It was found that circularization of RNA from Exon 2 of PVT1_212 reorganizes its reading frame, resulting into a novel open reading frame coding for 104 amino acids containing peptide, henceforth known as PEPc (PVT1 Encoded Peptide upon Circularization) or Conjoined (CJN). FIG. 34A shows a schematic diagram of the circularized of RNA with the open reading frame indicated, with the start codon (ATG) and the stop codon (TGA), encoding PEPc. A monoclonal antibody was developed against PEPc/CJN which can detect endogenously expressed PEPc/CJN in the four Hi-MYC cell lines (FIG. 34B). The specificity of the antibody was confirmed by carrying out a Western Blot analysis where inhibition of the CircPVT1 (by si_C2) but not of PVT1_212 (by si_3) resulted into reduction of the protein detected by the PEPc antibody (FIG. 34C).

Figure 35C:
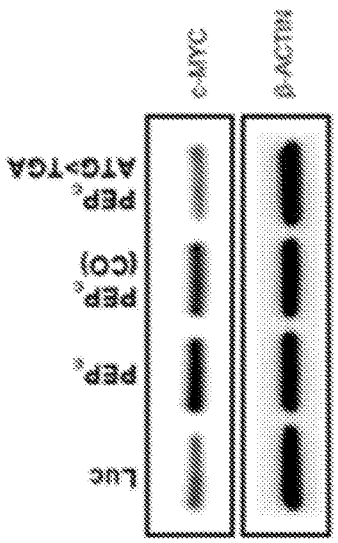
FIG. 35C and FIG. 35D represent western blot and quantitation for expression of c-MYC in PEPc constructs and control (Luciferase, Luc) expressing cells.
Figure 35D:
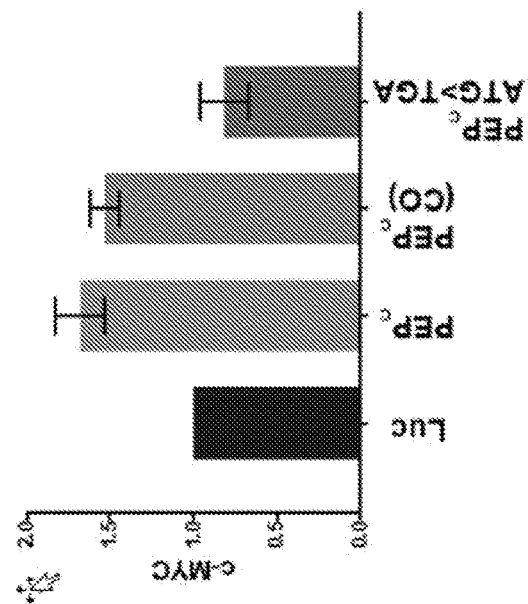
Figure 35A:
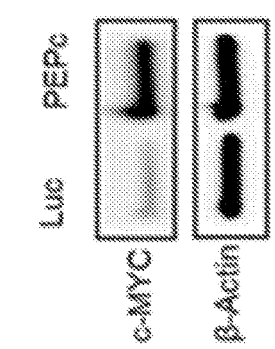
FIG. 35A shows representative western blot analysis of MYC protein in U2OS cells stably transfected with Luciferase (Luc; as control) or PEPc.
Figure 35B:
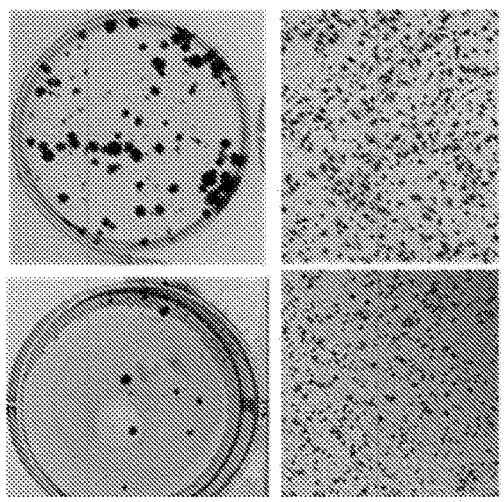
FIG. 35B shows representative data from colony formation and cell migration assay using Luc (as control) or PEPc.

Expression of PEPc is sufficient to augment MYC in cancer cells. Western blot analysis of MYC protein in U2OS cells stably transfected with Luciferase (as control) or PEPc, showed increase in MYC levels on ectopic expression of PEPc (FIG. 35A). PEPc expression increased colony formation and migration ability of U2OS (FIG. 35B). Soft agar assay showed an increase in colony numbers compared to the control when equal number of U2OS+Luciferase and U2OS+PEPc cells are plated on soft agar. Transwell migration assay showed increase in migration potential in U2OS+PEPc cells.

Additional sequences that may be used in the methods disclosed herein include those listed in Table 1, below.

| SEQ ID NO. | Sequence | Description |
|---|---|---|
| 1 | GCCTGATCTTTTGGCCAGAAGGAGATTAAAAAGATGCCC CTCAAGATGGCTGTGCCTGTCAGCTGCATGGAGCTTCGTT CAAGTATTTTCTGAGCCTGATGGATTTACAGTGATCTTCA GTGGTCTGGGGAATAACGCTGGTGGAACCATGCACTGGA ATGACACACGCCCGGCACATTTCAGGATACTAAAAGTGG TTTTAAGGGAGGCTGTGGCTGAATGCCTCATGGATTCTTA CAGCTTGGATGTCCATGGGGGACGAAGGACTGCAGCTGG CTGAGAGGGTTGAGATCTCTGTTTACTTAGATCTCTGCCA ACTTCCTTTGGGTCTCCCTATGGAATGTAAGACCCCGACT CTTCCTGGTGAAGCATCTGATGCACGTTCCATCCGGCGCT CAGCTGGGCTTGAG | Circular RNA of exon 2 of PVT1 splice variant PVT1_212 ("CircPVT1") |
| 2 | CCATCCGGCGCTCAG | Si_CircPVT1 or si_C2: Target sequence |
| 3 | UGGGCUUGAGGCCUGAUCUUU | Sense sequence for Si_CircPVT1 or si_C2: Target sequence |
| 4 | AGAUCAGGCCUCAAGCCCAUU | Antisense sequence for Si_CircPVT1 or si_C2: Target sequence |

| SEQ ID NO. | Sequence | Description |
|---|---|---|
| 5 | GCCATCATGATGGTACTTT | siRNA PVT1 Exon 3 target sequence |
| 6 | CAUCAUGAUGGUACUUUAATT | siRNA PVT1 Exon 3 sense strand |
| 7 | UUAAAGUACCAUCAUGAUGGC | siRNA PVT1 Exon 3 antisense strand |
| 8 | CCGGCACATTTCAGGATACTA | siRNA PVT1 Exon 2 target sequence |
| 9 | GGCACAUUUCAGGAUACUATT | siRNA PVT1 Exon 2 target sequence |
| 10 | UAGUAUCCUGAMUGUGCCGG | siRNA PVT1 Exon 2 target sequence |
| 11 | atgcacgttccatcc<br>ggcgctcagctgggcttgaggcctgatcttttggccagaaggaga<br>ttaaaaagatgcccctcaagatggctgtgcctgtcagctgcatgg<br>agcttcgttcaagtattttctgagcctgatggatttacagtgatc<br>ttcagtggtctggggaataacgctggtggaaccatgcactggaat<br>gacacacgcccggcacatttcaggatactaaaagtggttttaagg<br>gaggctgtggctgaatgcctcatggattcttacagcttggatgtc<br>catgggggacgaaggactgcagctggctga | CircPVT1's endogenously expressed 104 aa peptide ("PEPc" or "Conjoined") |
| 12 | M H V P S G A Q L G L R P D L<br>L A R R R L K R C P S R W L C<br>L S A A W S F V Q V F S E P D<br>G F T V I F S G L G N N A G G<br>T M H W N D T R P A H F R I L<br>K V V L R E A V A E C L M D S<br>Y S L D V H G G R R T A A G * | CircPVT1's endogenously expressed 104 aa peptide ("PEPc" or "Conjoined") |
| 13 | ATG CAC GTT CCA TCC GGC GCT CAG CTG GGC TTG<br>AGG CCT GAT CTT TTG GCC AGA AGG AGA TTA AAA<br>AGA TGC CCC TCA AGA TGG CTG TGC CTG TCA GCT<br>GCA TGG AGC TTC GTT CAA GTA TTT TCT GAG CCT GAT<br>GGA TTT ACA GTG ATC TTC AGT GGT CTG GGG AAT<br>AAC GCT GGT GGA ACC ATG CAC TGG AAT GAC ACA<br>CGC CCG GCA CAT TTC AGG ATA CTA AAA GTG GTT TTA<br>AGG GAG GCT GTG GCT GAA TGC CTC ATG GAT TCT<br>TAC AGC TTG GAT GTC CAT GGG GGA CGA AGG ACT<br>GCA GCT GGC TGA | Original PEPc DNA |
| 14 | MHVPSGAQLGLRPDLLARRRLKRCPSRWLCLSAAWSFVQV<br>FSEPDGFTVIFSGLGNNAGGTMHWNDTRPAHFRILKVVLRE<br>AVAECLMDSYSLDVHGGRRTAAG | Original PEPc aa (104 aa) |
| 15 | ATG CAT GTA CCT TCC GGC GCC CAA CTC GGC CTC AGA<br>CCG GAC CTG TTG GCC CGA CGA CGA CTG AAG CGA<br>TGC CCT AGC AGG TGG CTC TGT CTG TCA GCT GCG TGG<br>TCT TTT GTC CAA GTT TTC TCC GAG CCA GAT GGT TTC<br>ACA GTT ATT TTC TCC GGG TTG GGT AAC AAT GCG GGC<br>GGC ACT ATG CAT TGG AAT GAT ACT AGA CCA GCA<br>CAC TTT AGG ATC TTG AAA GTG GTC CTC AGG GAA<br>GCG GTG GCG GAA TGT CTG ATG GAT AGT TAT TCA<br>CTG GAC GTA CAT GGG GGT CGC CGA ACA GCC GCA<br>GGC TGA | Codon optimized PEPc DNA |
| 16 | TGA CAC GTT CCA TCC GGC GCT CAG CTG GGC TTG<br>AGG CCT GAT CTT TTG GCC AGA AGG AGA TTA AAA<br>AGA TGC CCC TCA AGA TGG CTG TGC CTG TCA GCT<br>GCA TGG AGC TTC GTT CAA GTA TTT TCT GAG CCT GAT<br>GGA TTT ACA GTG ATC TTC AGT GGT CTG GGG AAT<br>AAC GCT GGT GGA ACC TGA CAC TGG AAT GAC ACA<br>CGC CCG GCA CAT TTC AGG ATA CTA AAA GTG GTT TTA | PEPc (ATG > TGA) DNA |

| SEQ ID NO. | Sequence | Description |
|---|---|---|
| | AGG GAG GCT GTG GCT GAA TGC CTC TGA GAT TCT TAC AGC TTG GAT GTC CAT GGG GGA CGA AGG ACT GCA GCT GGC TGA | |

While preferred embodiments of the present disclosure have been shown and described herein, it will be obvious to those skilled in the art that such embodiments are provided by way of example only. It is not intended that the disclosed methods be limited by the specific examples provided within the specification. While the disclosed methods have been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all aspects of the disclosure are not limited to the specific depictions, configurations or relative proportions set forth herein which depend upon a variety of conditions and variables. It should be understood that various alternatives to the embodiments of the disclosed methods described herein may be employed in practicing the methods. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed is:

1. A method of identifying whether a subject is at risk for having a MYC-driven cancer, the method comprising:
   (a) obtaining a biological sample from the subject;
   (b) preparing cDNA from mRNA in the biological sample using primers comprising a sequence complementary to a circPVT1_212 splice variant (SEQ ID NO: 1) but not to a wild type form of PVT1 to produce prepared cDNA;
   (c) determining an expression level of the circPVT1_212 splice variant (SEQ ID NO: 1) in the biological sample; and
   (d) identifying whether the subject is at risk for having the MYC-driven cancer based on the expression level of the circPVT1_212 splice variant (SEQ ID NO: 1), wherein the MYC-driven cancer comprises a MYC-driven 8q24 gain medulloblastoma, wherein the MYC-driven 8q24 gain medulloblastoma comprises a subgroup 3, subgroup 4, Wnt, or Shh type medulloblastoma, and wherein the subject is stratified as having a subgroup 3 type medulloblastoma if circPVT1_212 splice variant expression level is 200 to 1000 fold elevated compared to a reference value, wherein the reference value is the expression level of circPVT1_212 splice variant in a non-tumor sample.

2. A method of identifying whether a subject is at risk for having a MYC-driven cancer, the method comprising:
   (a) obtaining a biological sample from the subject;
   (b) preparing cDNA from mRNA in the biological sample using primers comprising a sequence complementary to a circPVT1_212 splice variant (SEQ ID NO: 1) but not to a wild type form of PVT1 to produce prepared cDNA;
   (c) determining an expression level of the circPVT1_212 splice variant (SEQ ID NO: 1) in the biological sample; and
   (d) identifying whether the subject is at risk for having the MYC-driven cancer based on the expression level of the circPVT1_212 splice variant (SEQ ID NO: 1), wherein the MYC-driven cancer comprises a MYC-driven 8q24 gain medulloblastoma, wherein the MYC-driven 8q24 gain medulloblastoma comprises a subgroup 3, subgroup 4, Wnt, or Shh type medulloblastoma, and wherein the subject is stratified as having a subgroup 3, Wnt, or Shh type medulloblastoma if circPVT1_212 splice variant expression level is 15 to 200 fold elevated compared to a reference value, wherein the reference value is the expression level of circPVT1_212 splice variant in a non-tumor sample.

3. A method of identifying whether a subject is at risk for having a MYC-driven cancer, the method comprising:
   (a) obtaining a biological sample from the subject;
   (b) preparing cDNA from mRNA in the biological sample using primers comprising a sequence complementary to a circPVT1_212 splice variant (SEQ ID NO: 1) but not to a wild type form of PVT1 to produce prepared cDNA;
   (c) determining an expression level of the circPVT1_212 splice variant (SEQ ID NO: 1) in the biological sample; and
   (d) identifying whether the subject is at risk for having the MYC-driven cancer based on the expression level of the circPVT1_212 splice variant (SEQ ID NO: 1), wherein the MYC-driven cancer comprises a MYC-driven 8q24 gain medulloblastoma, wherein the MYC-driven 8q24 gain medulloblastoma comprises a subgroup 3, subgroup 4, Wnt, or Shh type medulloblastoma, and wherein the subject is stratified as having a subgroup 4 type medulloblastoma if circPVT1_212 splice variant expression level is 2 to 15 fold elevated compared to a reference value, wherein the reference value is the expression level of circPVT1_212 splice variant in a non-tumor sample.

4. The method of claim 1, further comprising measuring the expression level of PVT1_212 splice variant, PEP, or both, in the biological sample.

5. The method of claim 1, further comprising measuring the expression level of c- Myc, MYC, or both, in the biological sample.

6. The method of claim 2, further comprising measuring the expression level of PVT1_212 splice variant, PEP, or both, in the biological sample.

7. The method of claim 2, further comprising measuring the expression level of c- Myc, MYC, or both, in the biological sample.

8. The method of claim 3, further comprising measuring the expression level of PVT1_212 splice variant, PEP, or both, in the biological sample.

9. The method of claim 3, further comprising measuring the expression level of c- Myc, MYC, or both, in the biological sample.

* * * * *